US010907200B2

(12) United States Patent
Wu et al.

(10) Patent No.: US 10,907,200 B2
(45) Date of Patent: Feb. 2, 2021

(54) COMPOSITIONS AND METHODS FOR NUCLEIC ACID AMPLIFICATION

(71) Applicant: Ampliwise Inc., Santa Clara, CA (US)

(72) Inventors: Kai Wu, Mountain View, CA (US); Mindy Su, Cupertino, CA (US); Xing Su, Cupertino, CA (US)

(73) Assignee: Ampliwise Inc., Santa Clara, CA (US)

( * ) Notice: Subject to any disclaimer, the term of this patent is extended or adjusted under 35 U.S.C. 154(b) by 139 days.

(21) Appl. No.: 15/597,313

(22) Filed: May 17, 2017

(65) Prior Publication Data

US 2017/0327870 A1    Nov. 16, 2017

Related U.S. Application Data

(63) Continuation of application No. PCT/US2015/061312, filed on Nov. 18, 2015.

(60) Provisional application No. 62/082,534, filed on Nov. 20, 2014, provisional application No. 62/082,538, filed on Nov. 20, 2014, provisional application No. 62/082,541, filed on Nov. 20, 2014.

(51) Int. Cl.
*C12Q 1/6853* (2018.01)
*C12P 19/34* (2006.01)
*C12Q 1/6827* (2018.01)
*C12Q 1/686* (2018.01)

(52) U.S. Cl.
CPC ............ *C12Q 1/6853* (2013.01); *C12P 19/34* (2013.01); *C12Q 1/686* (2013.01); *C12Q 1/6827* (2013.01)

(58) Field of Classification Search
CPC ..... C12P 19/34; C12Q 1/6827; C12Q 1/6853; C12Q 1/686
See application file for complete search history.

(56) References Cited

U.S. PATENT DOCUMENTS

| | | | |
|---|---|---|---|
| 6,090,592 A | 7/2000 | Adams et al. | |
| 6,509,157 B1* | 1/2003 | Martinez | C12Q 1/6848 435/6.12 |
| 8,304,183 B2 | 11/2012 | Sooknanan | |
| 2002/0081583 A1 | 6/2002 | Abe et al. | |
| 2002/0137058 A1 | 9/2002 | Mirkin et al. | |
| 2003/0170711 A1 | 9/2003 | Brown et al. | |
| 2009/0325169 A1 | 12/2009 | Walder et al. | |
| 2010/0041053 A1* | 2/2010 | Fiss | C12Q 1/6853 435/5 |
| 2013/0310269 A1 | 11/2013 | So | |
| 2014/0162885 A1 | 6/2014 | Berka et al. | |
| 2014/0329245 A1* | 11/2014 | Spier | C12Q 1/686 435/6.12 |
| 2016/0046995 A1* | 2/2016 | Kochanczyk | C12Q 1/6827 506/9 |

FOREIGN PATENT DOCUMENTS

| | | |
|---|---|---|
| WO | WO-2016081549 A1 | 5/2016 |
| WO | WO-2016081551 A1 | 5/2016 |
| WO | WO-2016081585 A1 | 5/2016 |

OTHER PUBLICATIONS

Co-pending U.S. Appl. No. 15/597,305, filed May 17, 2017.
Co-pending U.S. Appl. No. 15/597,310, filed May 17, 2017.
International search report and written opinion dated Mar. 21, 2016 for PCT Application No. PCT/US15/61252.
International search report and written opinion dated Apr. 19, 2016 for PCT Application No. PCT/US15/61312.
International search report and written opinion dated Apr. 21, 2016 for PCT Application No. PCT/US15/61255.
Lin, et al. 3 '-5 ' Exonucleolytic Activity of DNA Polymerases: Structural Features That Allow Kinetic Discrimination between Ribo- and Deoxyribonucleotide Residues. Biochemistry 40:8749-8755, 2001.
"Algae," Wikipedia.com, accessed Mar. 4, 2016. (Year: 2016).
"Archaea," Wikipedia.com, accessed May 11, 2016. (Year: 2016).
"Fish," (Wikipedia.com, accessed Nov. 2, 2014).
Forster et al., "A human gut bacterial genome and culture collection for improved metagenomics analyses", Nature Biotechnology, vol. 37, Feb. 2019, pp. 186-192. (Year: 2019).
"Fungi," (Wikipedia.com; accessed Jun. 3, 2013).
"How many species of bacteria are there" (wisegeek.com; accessed Jan. 21, 2014).
"List of sequenced bacterial genomes" (Wikipedia.com; accessed Jan. 24, 2014).
Mammal. wikipedia.com, accessed Sep. 22, 2011.
"Murinae," (Wikipedia.com. Accessed Mar. 18, 2013.
Office action dated Mar. 1, 2019 for U.S. Appl. No. 15/597,305.
Office action dated Mar. 28, 2019 for U.S. Appl. No. 15/597,310.
"Plant," (Wikipedia.com; accessed Mar. 8, 2013).
"Protozoa," Wikipedia.com, accessed May 11, 2016. (Year: 2016).
Sharon Begley, "Psst, the human genome was never completely sequenced", STS News, Jun. 20, 2017. (Year: 2017).
Stratagene Catalog. 1988; p. 39. Gene Characterization Kits. Table of Contents.
"Viruses" (Wikipedia.com, accessed Nov. 24, 2012).

* cited by examiner

*Primary Examiner* — Teresa E Strzelecka
(74) *Attorney, Agent, or Firm* — Dave Law Group LLC; Raj S. Dave

(57) ABSTRACT

The disclosure provides compositions and methods for amplifying nucleic acids.

17 Claims, 22 Drawing Sheets

Specification includes a Sequence Listing.

A

```
2341 TGC CTC ACC TCC ACC GTG CAG CTC ATC ACG CAG CTC ATG CCC TTC 2385
2386 GGC TGC CTC CTG GAC TAT GTC CGG GAA CAC AAA GAC AAT ATT GGC 2430
2431 TCC CAG TAC CTG CTC AAC TGG TGT GTG CAG ATC GCA AAG GGC ATG 2475
2476 AAC TAC TTG GAG GAC CGT CGC TTG GTG CAC CGC GAC CTG GCA GCC 2520
2521 AGG AAC GTA CTG GTG AAA ACA CCG CAG CAT GTC AAG ATC ACA GAT 2565
2566 TTT GGG CTG GCC AAA CTG CTG GGT GCG GAA GAG AAA GAA
```

B

```
Forward primers
EG5:         CTC ACC TCC ACC GTG CAG CTC
EG5A:        CTC ACC TCC ACC GTG CAG CTC UTT TTT T
EG5U:        CTC ACC TCC ACC GTG CAG CTC UUU
EG5T:        CTC ACC TCC ACC GTG CAG CTC TTT Reverse primers
EG3:         CTT TCT CTT CCG CAC CCA GCA GT
EG3A:        CTT TCT CTT CCG CAC CCA GCA GTU TTT TTT
```

C

|      | EG5 | EG5A | EG5U | EG5T |
|------|-----|------|------|------|
| EG3  | 1   | 3    | 5    | 6    |
| EG3A |     | 2    | 4    |      |

Forward primers
EG21e5:        CAT GAA CTA CTT GGA GGA CCG T
EG21e5U1:      CAT GAA CTA CTT GGA GGA CCG TU
EG21e5U2:      CAT GAA CTA CTT GGA GGA CCG TUU
EG21e5U3:      CAT GAA CTA CTT GGA GGA CCG TUU U Reverse primers
EG21e3:        TC CAA TGC CAT CCA CTT GAT AG
EG21e3_isodC:  TC CAA TGC CAT CCA CTT GAT AG_iso-dC
EG21e3_isodG:  TC CAA TGC CAT CCA CTT GAT AG_iso-dG

B

|  | EG21e3 | EG21e3_isoC | EG21e3_isoG |
|---|---|---|---|
| EG21e5 | 00 | 0C | 0G |
| EG 21e5u1(1) | 10 | 1C | 1G |
| EG21e5u2(2) | 20 | 2C | 2G |
| EG21e5u3(3) | 30 |  |  |

```
Primer set
Forward: CAT GAA CTA CTT GGA GGA CCG TUU
Reverse:  TC CAA TGC CAT CCA CTT GAT AG_isodG_T
```

B

|            | 1  | 2     | 3  | 4  | 5  | 6     | 7  | 8  | 9  |
|------------|----|-------|----|----|----|-------|----|----|----|
| Taq        | 1x | 1x    | 1x | 1x |    | 1x    | 1x | 1x |    |
| Cloned Pfu |    | 0.25x | 1x | 2x | 2x |       |    |    |    |
| Deep vent  |    |       |    |    |    | 0.25x | 1x | 2x | 2x |

Target sequence:

5'TAGGACCCCTGCTCGTGTTACAGGCGGGGTTTTTCTTG
TTGACAAAATCCTCACAATACCACAGAGTCTAGACTCGT
GGTGGACTTCTCTCAATTTTCTAGGGGAACACCCGTGTG
TCTTGGCCAAAATTCGCAGTCCCAAATCTCCAGTCACTCA
CCAACCTGTTGTCCTCCAATTTGTCCTGGTTATCGCTGGA
TGTGTCTGCGGCGTTTATCATCTTCCTCTGCATCCTGCT
GCTATGCCTCATCTTCTTGTTGGTTCTTCTGGACTATCAA
GGTATGTTGCCCGTTTGTCCTCT-3'

B

Primers Without Molecular Moieties (N)

Forward:   TCCCAAATCTCCAGTCACTCA
Reverse:   CAACATACCTTGATAGTCCAG

Primers With Molecular Moieties (U)

Forward:   TCCCAAATCTCCAGTCACTCAUU
Reverse:   CAACATACCTTGATAGTCCAGUU

| Detection of SNP A | |
|---|---|
| A-reverse | 5' GCAGCAAGATGCCAAGCAUU |
| A-forward | 5' GGCTTCAACCATCCGTCIUU |

| Detection of SNP G | |
|---|---|
| G-forward | 5' CCC ATA ACC TCT GTT TCA CC UU |
| G-reverse | 5' AC CTC GAA CGT CGA GTA GTUUU |

SEQUENCE LISTING

```
<160> NUMBER OF SEQ ID NOS: 41

<210> SEQ ID NO 1
<211> LENGTH: 264
<212> TYPE: DNA
<213> ORGANISM: Homo sapiens

<400> SEQUENCE: 1
tgcctcacct ccaccgtgca gctcatcacg cagctcatgc ccttcggctg cctcctggac      60
tatgtccggg aacacaaaga caatattggc tcccagtacc tgctcaactg gtgtgtgcag     120
atcgcaaagg gcatgaacta cttggaggac cgtcgcttgg tgcaccgcga cctggcagcc     180
aggaacgtac tggtgaaaac accgcagcat gtcaagatca cagattttgg gctggccaaa     240
ctgctgggtg cggaagagaa agaa                                            264

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctcacctcca ccgtgcagct c                                                21

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

-continued

```
<223> OTHER INFORMATION: Description of Combined DNA/RNA Molecule:
      Synthetic primer

<400> SEQUENCE: 3
ctcacctcca ccgtgcagct cuttttt                                          28

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 4
ctcacctcca ccgtgcagct cuuu                                             24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcacctcca ccgtgcagct cttt                                             24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctttctcttc cgcacccagc agt                                              23

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 7
ctttctcttc cgcacccagc agtuttttt                                        30

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catgaactac ttggaggacc gt                                               22
```

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 9
catgaactac ttggaggacc gtu                                              23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 10
catgaactac ttggaggacc gtuu                                             24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 11
catgaactac ttggaggacc gtuuu                                            25

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccaatgcca tccacttgat ag                                               22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tccaatgcca tccacttgat agc                                              23

<210> SEQ ID NO 14
<211> LENGTH: 23
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 14
tccaatgcca tccacttgat agg                                          23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 15
catgaactac ttggaggacc gtuu                                         24

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccaatgcca tccacttgat agt                                          23

<210> SEQ ID NO 17
<211> LENGTH: 301
<212> TYPE: DNA
<213> ORGANISM: Unknown
<220> FEATURE:
<223> OTHER INFORMATION: Description of Unknown:
      target sequence

<400> SEQUENCE: 17
taggacccct gctcgtgtta caggcggggt ttttcttgtt gacaaaaatc ctcacaatac     60
cacagagtct agactcgtgg tggacttctc tcaatttttct agggggaaca cccgtgtgtc   120
ttggccaaaa ttcgcagtcc caaatctcca gtcactcacc aacctgttgt cctccaattt   180
gtcctggtta tcgctggatg tgtctgcggc gttttatcat cttcctctgc atcctgctgc   240
tatgcctcat cttcttgttg gttcttctgg actatcaagg tatgttgccc gtttgtcctc   300
t                                                                  301

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcccaaatct ccagtcactc a                                            21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                                        -continued
        primer

<400> SEQUENCE: 19
caacatacct tgatagtcca g                                              21

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 20
tcccaaatct ccagtcactc auu                                            23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 21
caacatacct tgatagtcca guu                                            23

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 22
aatacaggca tgactctcct uu                                             22

<210> SEQ ID NO 23
<211> LENGTH: 30
<212> TYPE: DNA
<213> ORGANISM: Unknown
<220> FEATURE:
<223> OTHER INFORMATION: Description of Unknown:
      target sequence

<400> SEQUENCE: 23
ccagaataca ggcatgactc tcctgattgt                                     30

<210> SEQ ID NO 24
<211> LENGTH: 29
<212> TYPE: DNA
<213> ORGANISM: Unknown
<220> FEATURE:
<223> OTHER INFORMATION: Description of Unknown:
      target sequence

<400> SEQUENCE: 24
tgattaggag agctaataat gtcctaaaa                                      29
```

<210> SEQ ID NO 25
<211> LENGTH: 21
<212> TYPE: DNA
<213> ORGANISM: Unknown
<220> FEATURE:
<223> OTHER INFORMATION: Description of Unknown:
    target sequence

<400> SEQUENCE: 25
tctatgaagt gtttgaaaaa t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 26
atgattttca aacacttcat a                                              21

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Description of Combined DNA/RNA Molecule:
    Synthetic primer

<400> SEQUENCE: 27
ttaggacatt attagctctc ctaatcuu                                       28

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
    primer
<220> FEATURE:
<223> OTHER INFORMATION: Description of Combined DNA/RNA Molecule:
    Synthetic primer

<400> SEQUENCE: 28
cagaatatag gcatgattct ccauu                                          25

<210> SEQ ID NO 29
<211> LENGTH: 30
<212> TYPE: DNA
<213> ORGANISM: Unknown
<220> FEATURE:
<223> OTHER INFORMATION: Description of Unknown:
    target sequence

<400> SEQUENCE: 29
ccagaatata ggcatgattc tccagactgt                                     30

<210> SEQ ID NO 30
<211> LENGTH: 29
<212> TYPE: DNA
<213> ORGANISM: Unknown
<220> FEATURE:
<223> OTHER INFORMATION: Description of Unknown:

target sequence

<400> SEQUENCE: 30
taattaggag ggcaaacaat gtcttaaaa                                         29

<210> SEQ ID NO 31
<211> LENGTH: 21
<212> TYPE: DNA
<213> ORGANISM: Unknown
<220> FEATURE:
<223> OTHER INFORMATION: Description of Unknown:
      target sequence

<400> SEQUENCE: 31
tttatgaagt gtttgaaaaa c                                                 21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 32
acattgtttg ccctcctaat tuu                                               23

<210> SEQ ID NO 33
<211> LENGTH: 215
<212> TYPE: DNA
<213> ORGANISM: Unknown
<220> FEATURE:
<223> OTHER INFORMATION: Description of Unknown:
      target sequence
<220> FEATURE:
<221> NAME/KEY: modified_base
<222> LOCATION: (127)..(127)
<223> OTHER INFORMATION: a, c, t, g, unknown or other

<400> SEQUENCE: 33
catgtggacc ccgtggttgt gtttgacttc gctagcttat accccagcat tatccaggcc       60
cataacctct gtttcaccac cctggcgctc gatgaagtgg atctggccgg gcttcaacca      120
tccgtcnact actcgacgtt cgaggtggtg ggtgaccaaa agttattttt tgtccacgcc      180
catattcgcg aaagcctgct tggcatcttg ctgcg                                 215

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 34
gcagcaagat gccaagcauu                                                   20

<210> SEQ ID NO 35
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (18)..(18)
<223> OTHER INFORMATION: Inosine

<400> SEQUENCE: 35
ggcttcaacc atccgtcnuu                                                   20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 36
cccataacct ctgtttcacc uu                                                22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 37
acctcgaacg tcgagtagtu uu                                                22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 38
cgggcttcaa ccatccgtca au                                                22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 39
cgggcttcaa ccatccgtca uu                                                22
```

```
<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 40
cgggcttcaa ccatccgtcg au                                             22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 41
cgggcttcaa ccatccgtcg uu                                             22
```

COMPOSITIONS AND METHODS FOR NUCLEIC ACID AMPLIFICATION

CROSS-REFERENCE

This application is a continuation of PCT International Application No. PCT/US2015/061312, filed Nov. 18, 2015, which claims priority to U.S. Provisional Patent Application No. 62/082,534 filed on Nov. 20, 2014, U.S. Provisional Patent Application No. 62/082,538 filed on Nov. 20, 2014 and U.S. Provisional Patent Application No. 62/082,541 filed on Nov. 20, 2014, which applications are herein incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Jul. 13, 2017, is named 46846703301SL.txt and is 12,196 bytes in size.

BACKGROUND

Nucleic acid amplification methods permit amplification of nucleic acid molecules in a sample, such as a biological sample. A nucleic acid molecule can be amplified, via, for example, thermal cycling based approaches (e.g., polymerase chain reaction (PCR)) or via isothermal approaches. Nucleic acid amplification may also be useful in preparing a nucleic acid molecule for subsequent analysis in numerous applications related to nucleic acid analysis such as, for example in detecting target nucleic acid sequences, detecting rare nucleic acid molecules/sequences in a sample and/or preparing a nucleic acid molecule for a sequencing reaction. However, nucleic acid amplification reactions can generate non-specific amplification products such as primer dimer by-products that can reduce the efficiency and/or specificity of a nucleic acid amplification reaction. Thus, due to the applicability of nucleic acid amplification to a wide range of applications, there exists a need for compositions and methods useful for amplifying nucleic acid molecules that aid in minimizing the generation of non-specific amplification products during nucleic acid amplification.

SUMMARY

The disclosure provides compositions and methods for the amplification and analysis of nucleic acids.

An aspect of the disclosure provides a primer having a length from about 6 to 60 nucleotides. The primer can comprise, from a 5' end to 3' end, a nucleotide sequence A that is substantially complementary to a target nucleic acid molecule and a molecular moiety at the 3' end that is non-complementary with respect to one or more corresponding nucleotides of the target nucleic acid molecule. The 3' end can be adapted to be extended in a primer extension reaction to form a complement nucleic acid strand of the target nucleic acid molecule only upon removal of the molecular moiety.

In some embodiments, the primer may be a hairpin loop primer characterized in that the nucleotide sequence A exhibits sequence complementarity to itself and/or a respective molecular moiety. In some embodiments, the primer may be an isolated and purified nucleic acid strand. In some embodiments, the 3' end may be cleavable by an enzyme with 3' to 5' exonuclease activity. In some embodiments, the primer may be adapted for use in a reverse transcription polymerase chain reaction (RT-PCR).

In some embodiments, the molecular moiety may comprise nucleotide sequence B having 1-10 consecutive nucleotides that are non-complementary with respect to 1-10 corresponding nucleotides of the target nucleic acid molecule. In some embodiments, the nucleotide sequence A may be of a length that provides sufficient complementarity with respect to the target nucleic acid molecule.

In some embodiments, the molecular moiety may be at least one nucleotide, nucleotide analogue or non-nucleotide species. In some embodiments, the molecular moiety may comprise a phosphodiester bond or may be an n-phosphate moiety, where 'n' is greater than or equal to 1. In some embodiments, the molecular moiety may be adapted to prevent the formation of a primer dimer molecular complex comprising the primer. In some embodiments, the primer can have a length from 6 to 20 nucleotides. In some embodiments, the molecular moiety can have a length that is from 1 to 10 individual species. In some embodiments, the molecular moiety may comprise a nucleotide analogue having an unnatural base or no base. In some embodiments, the primer may be suitable for use in single nucleotide polymorphism detection.

In some embodiments, the primer is included in a primer set that comprises at least one additional primer exhibiting sequence complementary to a complement nucleic acid strand of the target nucleic acid molecule. In some embodiments, the primer set, when used in an amplification reaction in the presence of a polymerase having 3' to 5' exonuclease activity, can yield amplified target nucleic acids that are substantially free of primer dimer by-products. In some embodiments, primer dimer by-products can be present at a concentration that is less than about 10% of the amplified target nucleic acids as measured by a melting curve of the amplified target nucleic acids. In some embodiments, the primer may be included in a solution. In some embodiments, the primer may comprise at least one stopper nucleotide that may be, for example, nuclease resistant.

An additional aspect of the disclosure provides a primer set comprising a forward primer and reverse primer. Each of the forward and reverse primers from a 5' end to 3' end can comprise a nucleotide sequence A that is substantially complementary to a target nucleic acid molecule or a complement thereof and a molecular moiety at a 3' end that is non-complementary with respect to one or more corresponding nucleotides of the target nucleic acid molecule or the complement. A molecular moiety of the forward primer and a molecular moiety of the reverse primer may not be complementary to each other. Moreover, the forward primer and reverse primer can be extendable in a template-directed manner only upon removal of the molecular moiety.

In some embodiments, the forward primer and/or reverse primer may be a hairpin loop primer characterized in that the sequence A exhibits sequence complementarity to itself and/or a respective molecular moiety. In some embodiments, the forward and reverse primers may be isolated and purified nucleic acid strands. In some embodiments, the 3' end may be cleavable by an enzyme with 3' to 5' exonuclease activity. In some embodiments, the forward primer and/or reverse primer may be adapted for use in a reverse transcription polymerase chain reaction (RT-PCR).

In some embodiments, the molecular moiety can comprise a nucleotide sequence B having 1-10 consecutive nucleotides that are non-complementary with respect to 1-10 corresponding nucleotides of the target nucleic acid molecule or the complement. In some embodiments, the nucleotide sequence A can be of a length that provides sufficient complementarity with respect to the target nucleic acid molecule or the complement.

In some embodiments, the molecular moiety may be at least one nucleotide, nucleotide analogue or non-nucleotide species. In some embodiments, the molecular moiety may comprise a phosphodiester bond or is an n-phosphate moiety, where 'n' is greater than or equal to 1. In some embodiments, the molecular moiety may be adapted to prevent the formation of a primer dimer molecular complex comprising the forward primer and/or the reverse primer. In some embodiments, the forward primer and/or reverse primer may have a length from 6 to 20 nucleotides. In some embodiments, the molecular moiety may have a length that is from 1 to 10 individual species. In some embodiments, the molecular moiety may comprise a nucleotide analogue having an unnatural base or no base. In some embodiments, the forward primer and/or reverse primer may be suitable for use in single nucleotide polymorphism detection. In some embodiments, the primer set is included in a solution. In some embodiments, the forward and/or the reverse primer may comprise at least one stopper nucleotide that may be, for example, nuclease resistant.

An additional aspect of the disclosure provides a method for nucleic acid amplification. The method can comprise annealing a forward primer to a single-stranded target nucleic acid molecule and a reverse primer to a complement of the single-stranded target nucleic acid molecule. Each of the forward and reverse primers from a 5' end to 3' end can comprise a molecular moiety at a 3' end that is non-complementary with respect to one or more corresponding nucleotides of the single-stranded target nucleic acid molecule or the complement. Moreover, a molecular moiety of the forward primer and a molecular moiety of the reverse primer may not be complementary to each other. The method further comprises extending the forward primer and the reverse primer in a template-directed manner to yield double-stranded target nucleic acid molecules. The method further comprises denaturing the double-stranded target nucleic acid molecules to generate single-stranded target nucleic acid molecules. Annealing of the forward and reverse primers, extension of the forward and reverse primers and denaturing the resulting double-stranded target nucleic acid molecules can be repeated for at least one cycle to yield amplified double-stranded target nucleic acid molecules.

In some embodiments, after the at least one cycle, primer dimer by-products comprising the forward primer and/or the reverse primer may be present at a concentration that is less than about 10% of the amplified double-stranded target nucleic acid molecules as measured by a melting curve analysis of the amplified double-stranded target nucleic acid molecules.

In some embodiments, the method may be performed in partition such as, for example, a well or a droplet. In some embodiments, the method further comprises detecting at least a subset of the amplified double-stranded target nucleic acid molecules. The detecting may comprise, for example, optical detection, electrostatic detection, or electrochemical detection. In some embodiments, the method further comprises removing the molecular moiety of the forward primer and the molecular moiety of the reverse primer prior to extending the forward and reverse primers. In some embodiments, the forward primer and/or reverse primer may comprise at least one stopper nucleotide that may be, for example, nuclease resistant.

An additional aspect of the disclosure provides a method for nucleic acid amplification. The method can comprise subjecting a reaction mixture containing a nucleic acid sample having a single-stranded target nucleic acid molecule to a nucleic acid amplification reaction under conditions to yield an amplified product of the nucleic acid sample. The reaction mixture can comprise a forward primer that is complementary to the single-stranded target nucleic acid molecule and comprises a first molecular moiety at a 3' end that is non-complementary with respect to one or more corresponding nucleotides of the single-stranded target nucleic acid molecule. The reaction mixture can also comprise a reverse primer that is complementary to a complement of the single-stranded target nucleic acid molecule and comprises a second molecular moiety at a 3' end that is non-complementary with respect to one or more corresponding nucleotides of the complement. The first molecular moiety and the second molecular moiety may not be complementary to each other.

In some embodiments, the subjecting can comprise extending the forward primer and the reverse primer in a template-directed manner to yield double-stranded target nucleic acid molecules. In some embodiments, the subjecting can comprise removing the first and second molecular moieties prior to extending the forward primer and the reverse primer. In some embodiments, the first and/or second molecular moieties may be removable with the aid of a 3' to 5' exonuclease activity of a polymerase in the reaction mixture.

In some embodiments, the forward and/or reverse primer can be an isolated and purified nucleic acid strand. In some embodiments, the forward primer and/or reverse primer may be a hairpin loop primer characterized in that the sequence A exhibits sequence complementarity to itself and/or the first and/or second molecular moiety. In some embodiments, the forward primer and/or reverse primer may be adapted for use in a reverse transcription polymerase chain reaction (RT-PCR).

In some embodiments, each of the forward and reverse primers from a 5' end to 3' end can comprise a nucleotide sequence A that is substantially complementary to the single-stranded target nucleic acid molecule or the complement. In some embodiments, the first or second molecular moiety may comprise a nucleotide sequence B having 1-10 consecutive nucleotides that are non-complementary with respect to 1-10 corresponding nucleotides of the target nucleic acid molecule or the complement. In some embodiments, the nucleotide sequence A may be of a length that provides sufficient complementarity with respect to the target nucleic acid molecule or the complement.

In some embodiments, the first and/or second molecular moiety may be at least one nucleotide, nucleotide analogue or non-nucleotide species. In some embodiments, the first and/or second molecular moiety may comprise a phosphodiester bond or is an n-phosphate moiety, where 'n' is greater than or equal to 1. In some embodiments, the first and/or second molecular moiety may be adapted to prevent the formation of a primer dimer molecular complex comprising the forward primer and/or the reverse primer.

In some embodiments, the forward primer and/or reverse primer can have a length from 6 to 60 nucleotides. In some embodiments, the molecular moiety can have a length that is from 1 to 10 individual species. In some embodiments, the first and/or second molecular moiety may comprise a nucleotide analogue having an unnatural base or no base. In some embodiments, the forward primer and/or reverse primer may be suitable for use in single nucleotide polymorphism detection. In some embodiments, a temperature of the reaction mixture may be controlled with aid of a thermal gradient. In some embodiments, the forward primer and/or reverse primer may comprise at least one stopper nucleotide that may be, for example, nuclease resistant.

An additional aspect of the disclosure provides a method for nucleic acid amplification. The method can comprise providing a reaction mixture comprising a forward primer, a reverse primer and a target nucleic acid molecule, wherein the forward primer is complementary to the target nucleic acid molecule and the reverse primer is complementary to a complement of the target nucleic acid molecule. The method can further comprise, using the forward primer and the reverse primer, performing multiple amplification cycles to generate amplified products of the target nucleic acid molecule in solution. After 20 or more amplification cycles, a concentration of a primer dimer molecular complex comprising a sequence of the forward primer and/or a sequence of the reverse primer in the reaction mixture can less than about 10% of the amplified products as determined by a melting curve analysis of the amplified products.

In some embodiments, the multiple amplification cycles are performed with the aid of a thermal gradient. In some embodiments, the method can further comprise detecting the amplified products. In some embodiments, the cycle threshold (Ct) for detecting the amplified products may be less than 60. In some embodiments, the forward primer may comprise a molecular moiety at a 3' end that is non-complementary with respect to the target nucleic acid molecule. In some embodiments, the reverse primer may comprise a molecular moiety at a 3' end that is non-complementary with respect to a complement of the target nucleic acid molecule. In some embodiments, the primer dimer molecular complex may be undetectable. In some embodiments, the forward primer and/or the reverse primer may comprise at least one stopper nucleotide that may be, for example, nuclease resistant.

An additional aspect of the disclosure provides an oligonucleotide comprising about 6 to 60 nucleotides. A 3' end of the oligonucleotide can have a molecular moiety that is non-binding with respect to a target nucleic acid molecule, is recognizable by a polymerase having 3' to 5' exonuclease activity, and is cleavable by the 3' to 5' exonuclease activity of the polymerase during amplification of the target nucleic acid molecule.

In some embodiments, the oligonucleotide may comprise about 10 to 60 nucleotides. In some embodiments, the oligonucleotide may comprise a nucleotide sequence A that exhibits sequence complementarity to itself and/or the molecular moiety. In some embodiments, the nucleotide sequence A may be of a length that provides sufficient complementarity with respect to the target nucleic acid molecule. In some embodiments, the molecular moiety may comprise a nucleotide sequence B having 1-10 consecutive nucleotides that are non-complementary with respect to 1-10 corresponding nucleotides of the target nucleic acid molecule.

In some embodiments, the oligonucleotide may be an isolated and purified nucleic acid strand. In some embodiments, the oligonucleotide may be adapted for use in a reverse transcription polymerase chain reaction (RT-PCR). In some embodiments, the molecular moiety may be at least one nucleotide, nucleotide analogue or non-nucleotide species. In some embodiments, the molecular moiety may comprise a phosphodiester bond or may be an n-phosphate moiety, where 'n' is greater than or equal to 1. In some embodiments, the molecular moiety may be adapted to prevent the formation of an oligonucleotide dimer by-product comprising the oligonucleotide. In some embodiments, the oligonucleotide may have a length from 6 to 20 nucleotides. In some embodiments, the molecular moiety may have a length that is from 1 to 10 individual species. In some embodiments, the molecular moiety may comprise a nucleotide analogue having an unnatural base or no base. In some embodiments, the oligonucleotide may be suitable for use in single nucleotide polymorphism detection. In some embodiments, the oligonucleotide may be included in a solution. In some embodiments, the oligonucleotide may comprise at least one stopper nucleotide that may be, for example, nuclease resistant.

In some embodiments, the oligonucleotide may be included in an oligonucleotide set comprising at least one additional oligonucleotide exhibiting sequence complementary to a complement nucleic acid strand of the target nucleic acid molecule. In some embodiments, the oligonucleotide set, when used in an amplification reaction in the presence of a polymerase having 3' to 5' exonuclease activity, can yield amplified target nucleic acids that are substantially free of oligonucleotide dimer by-products. In some embodiments, oligonucleotide dimer by-products may be present at a concentration that is less than about 10% as measured by a melting curve of the amplified target nucleic acids, when said oligonucleotide set is used in the amplification reaction.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 3 (panel B) and FIG. 3 (panel C) are schematics depicting example methods for detecting the example SNPs depicted in FIG. 3 (panel A);

FIG. 4 (panel B) provides forward and reverse primers (SEQ ID NOS: 2-7, respectively, in order of appearance) as described in Example 1; FIG. 4 (panel C) is a table describing different test reaction mixtures as described in Example 1; FIG. 4 (panel D) is a photograph of an example gel electrophoresis analysis as described in Example 1;

FIG. 5 (panel B) is a table describing different test reaction mixtures as described in Example 2; FIG. 5 (panel C) is a photograph of an example gel electrophoresis analysis as described in Example 2;

FIG. 6 (panel B) is a table describing different test reaction mixtures as described in Example 3; FIG. 6 (panel C) is a photograph of an example gel electrophoresis analysis as described in Example 3;

FIG. 7 (panel B) provides forward and reverse primers (SEQ ID NOS: 18-21, respectively, in order of appearance) as described in Example 4; FIG. 7 (panel C) is a photograph of an example gel electrophoresis analysis as described in Example 4;

FIG. 8 (panel B) is a photograph of an example gel electrophoresis analysis as described in Example 5;

FIG. 9 (panel B) a schematic depiction of a hairpin loop reverse transcription primer (SEQ ID NO: 26) as described in Example 6; FIG. 9 (panel C) is a photograph of an example gel electrophoresis analysis as described in Example 6;

FIG. 10 (panel B) provides example forward and reverse primers (SEQ ID NOS: 34-37, respectively, in order of appearance) as described in Example 7; FIGS. 10 (panel C) and 10 (panel D) provide graphic depictions of example melting curve analyses of various reaction mixtures and tables summarizing the contents of the various reaction mixtures as described in Example 7;

DETAILED DESCRIPTION

Figure 1:
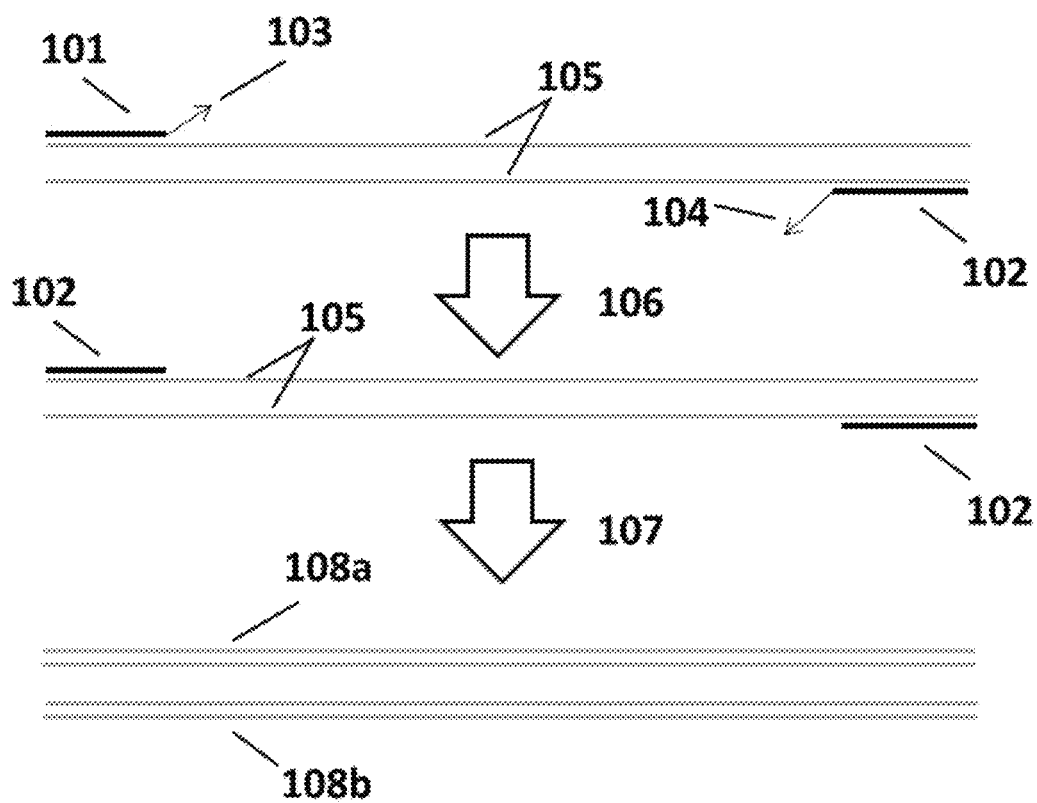
FIG. 1 is a schematic depicting an example method for nucleic acid amplification.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular form "a", "an" and "the" include plural references unless the context clearly dictates otherwise. For example, the term "a nucleic acid molecule" includes a plurality of nucleic acid molecules, including mixtures thereof.

As used herein, the terms "amplifying" and "amplification" are used interchangeably and generally refer to producing one or more copies of a nucleic acid. An "amplification reaction" generally refers to a reaction in which amplification of a nucleic acid occurs.

As used herein, the terms "anneal" and "annealing" generally refer to the binding of one nucleic acid molecule (e.g., a primer) with another nucleic acid molecule (e.g., a template nucleic acid molecule) via complementarity between the nucleic acid molecules.

"Complementarity", "complementary" and "sequence complementarity" generally refer to the ability of a nucleic acid to form hydrogen bond(s) with another nucleic acid by either Watson-Crick or other types of base-pairing. Sequence complementarity can aid in maintaining the structure stability of base-paired nucleic acid molecules via base stacking. A "complement" of a nucleic acid strand generally refers to another strand of nucleic acid that is complementary to the nucleic acid strand In some cases, a nucleic acid sequence can be complementary to itself in that one sequence region of the nucleic acid is complementary to another sequence region of the nucleic acid. "Partially complementary" generally means that a portion of a first nucleic acid sequence will hydrogen bond with a portion of a second nucleic acid sequence. "Substantially complementary" or "substantial complementarity" generally refers to a degree of complementarity that is at least 60%, 65%, 70%, 75%, 80%, 85%, 90%, 95%, 97%, 98%, 99%, or 100% over a region of 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more nucleotides. "Sufficient complementarity" generally refers to a degree of complementarity between two nucleic acid molecules (or two complementary regions of a single nucleic acid molecule) such that when the two nucleic acid molecules (or two complementary regions of the single nucleic acid molecule) hybridize via complementarity a stable complex is generated. In some cases, such a stable complex may have a melting temperature at about ambient temperature.

As used herein, the term "cycle threshold" or "Ct" generally refers to the cycle during an amplification reaction in which an increase in a detectable signal due to amplified product or amplified nucleic acid molecules reaches a statistically significant level above background signal.

As used herein, the terms "denaturing" and "denaturation" are used interchangeably and generally refer to the full or partial unwinding of the helical structure of a double-stranded nucleic acid, and in some embodiments the unwinding of the secondary structure of a single stranded nucleic acid.

As used herein, a "detectable species" generally refers to a composition that yields a detectable signal, the presence or absence of which can be used to detect the presence of a nucleic acid and/or copies of a nucleic acid. In some embodiments, a detectable species may be an optically-responsive species. As used herein, the term "optically-responsive species" generally refers to a detectable species that yields a detectable signal in the presence (or absence) of electromagnetic radiation, such as, for example, light.

As used herein, the term "melting temperature" ($T_m$) generally refers to the temperature at which two single-stranded nucleic acid molecules that are hybridized and form a double-stranded molecule dissociate from each other. In some embodiments, a melting temperature can refer to a temperature at which about 5%, 10%, 15%, 20%, 25%, 30%, 35%, 40%, 45%, 50%, 55%, 60%, 65%, 70%, 75%, 80%, 85%, 90%, 95%, 99% or more identical nucleic acid strands of a population of identical double-stranded nucleic acid molecules dissociate from their respective complement strands. For example, the melting temperature of a primer or molecular moiety may refer to the temperature at which about half of the molecules of the primer or molecular moiety in a population of identical primers or molecular moieties hybridized to a nucleic acid molecule dissociate from their complementary sequence on their respective nucleic acid molecules. A melting temperature of a nucleic acid molecule can be calculated based on the sequence of the nucleic acid molecule via any suitable calculation method.

In some embodiments, the melting temperature of a primer or molecule moiety may be about 20° C., 21° C., 22° C., 23° C., 24° C., 25° C., 26° C., 27° C., 28° C., 29° C., 30° C., 31° C., 32° C. 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., or higher.

As used herein, the term "molecular complex" generally refers to a complex comprising a plurality of nucleic acid molecules complexed together. Nucleic acid molecules of a molecular complex can be complexed together via binding interactions (e.g., non-specific binding, hybridization) between the nucleic acid molecules or can be complexed together via the extension or amplification (e.g., via an enzyme) of one or both of the nucleic acid molecules using, for example, the other as a template. One example of a molecular complex is a "primer dimer by-product" that comprises at least two or more primers (or a primer and one or more copies of another primer) complexed together. In another example, a primer dimer by-product can be an amplified product resulting from enzymatic extension of one or more primers. For example, a primer dimer by-product may comprise a forward primer bound with a reverse primer. In another example, a primer dimer by-product may comprise a first primer that has been extended to include the complementary sequence of a second primer. In some cases, such a primer dimer by-product may also include the second primer that has been extended to include the complementary sequence of the first primer. A primer dimer by-product can be generated during a nucleic acid amplification reaction when one or more primers in an amplification reaction mixture bind to another primer and/or are extended using another primer as a template rather than the target nucleic acid molecule.

Another example of a molecular complex is an "oligonucleotide dimer by-product" that comprises at least two or more oligonucleotides (or an oligonucleotide and one or more copies of another oligonucleotide) complexed together. For example, an oligonucleotide dimer by-product may comprise two or more oligonucleotides bound together. In another example, an oligonucleotide dimer by-product can be an amplified product resulting from enzymatic extension of one or more oligonucleotide species. In another example, an oligonucleotide dimer by-product may comprise a first oligonucleotide that has been extended to include the complementary sequence of a second oligonucleotide. In some cases, such an oligonucleotide dimer by-product may also include the second oligonucleotide that has been extended to include the complementary sequence of the first oligonucleotide. An oligonucleotide dimer by-product can be generated during a nucleic acid amplification reaction when one or more oligonucleotides in an amplification reaction mixture bind to another oligonucleotide and/or are extended using another oligonucleotide as a template rather than the target nucleic acid molecule. In general, a primer dimer by-product or an oligonucleotide by-product can be less than about 100 base pairs in length as measured, for example, via gel electrophoresis.

As used herein, the term "nucleic acid" and "nucleic acid molecule" are used interchangeably and generally refer to a polymeric form of nucleotides of any length, that can be deoxyribonucleotides (dNTPs), ribonucleotides (rNTPs), analogues thereof and/or combinations thereof. Nucleic acids may have any three dimensional structure, and may perform any function, known or unknown. Non-limiting examples of nucleic acids include deoxyribonucleic acid (DNA), ribonucleic acid (RNA), a peptide nucleic acid (PNA), a locked nucleic acid (LNA), fluorinated nucleic acids (FNA), bridged nucleic acids (BNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogues. If present, modifications to the nucleotide structure may be made before or after assembly of the nucleic acid. The sequence of nucleotides of a nucleic acid may be interrupted by non-nucleotide components such as for example, linker or spacer species. In some embodiments, the sequence of nucleotides may be interrupted by artificial non-pairing nucleotide analogues. A nucleic acid may be further modified after polymerization, such as by conjugation or binding with a detectable species. In some embodiments, a nucleic acid may be a primer that, in some embodiments, can be used to amplify another nucleic acid molecule.

In some embodiments, a nucleic acid molecule, including a to-be-amplified nucleic acid molecule such as, for example, a target nucleic acid molecule may be provided to a reaction mixture from a biological sample and amplified without purification. Non-limiting examples of biological samples include whole blood, dried blood (e.g., a dried blood spot), serum, saliva, semen, sputum, cerebrospinal fluid, urine, feces, cultured cells, animal tissue, plant tissue, a bodily fluid or other biological liquids and solids that are suspected of having a target nucleic acid molecule.

As used herein, the term "primer" generally refers to a nucleic acid molecule that is capable of hybridizing with a template nucleic acid molecule and capable of being extended in a template-directed manner via the template nucleic acid molecule.

A "primer extension reaction" generally refers to the binding (e.g., "annealing") of a primer to a strand of nucleic acid, followed by incorporation of nucleotides to the primer (e.g., "extension" of or "extending" the primer) often at its 3' end, using the strand of nucleic acid as a template. A primer extension reaction may be completed with the aid of an enzyme, such as, for example a polymerase.

As used herein, the term "reaction mixture" or "amplification reaction mixture" generally refer to a composition comprising one or more reagents necessary to complete a primer extension reaction and/or nucleic acid amplification, with non-limiting examples of such reagents that include one or more primers having specificity for a target nucleic acid, a polymerase, suitable buffers, co-factors (e.g., divalent and monovalent cations), nucleotides (e.g., deoxyribonucleotides (dNTPs)), and any other enzymes. In some embodiments, a reaction mixture can also comprise one or more detectable species.

As used herein, the term "target nucleic acid" or "target nucleic acid molecule" are used interchangeably and generally refer to a nucleic acid molecule in a starting population of nucleic acid molecules having a target sequence whose presence, amount, and/or nucleotide sequence, or changes in one or more of these, are desired to be determined. In some embodiments, a target nucleic acid molecule may be double-stranded. In some embodiments, a target nucleic acid molecule may be single-stranded. A target nucleic acid molecule may be a portion of a gene, a regulatory sequence, genomic DNA, cDNA, RNA including mRNA, miRNA, rRNA, or others. The target nucleic acid molecule may be a target nucleic acid molecule from a sample or a secondary target such as a product of an amplification reaction.

Various aspects of the disclosure provide primers, oligonucleotides, primer sets and oligonucleotide sets that can be useful in conducting nucleic acid amplification reactions. A primer or primer of a primer set and/or an oligonucleotide or oligonucleotide of an oligonucleotide set may comprise a molecular moiety at its 3' end that can be removed such that the primer or oligonucleotide may participate in a nucleic acid amplification reaction. Moreover, a molecular moiety can be useful in preventing the formation of primer dimer by-products or oligonucleotide by-products during a nucleic acid amplification reaction.

An aspect of the disclosure provides a primer that can have a length from about 6 to 60 nucleotides. The primer can comprise, from a 5' end to 3' end, a nucleotide sequence A that is substantially complementary to a target nucleic acid molecule; and a molecular moiety at its 3' end. The molecular moiety can be non-complementary with respect to one or more corresponding nucleotides of the target nucleic acid molecule. Moreover, the 3' end can be adapted to be extended in a primer extension reaction to form a complement nucleic acid strand of the target nucleic acid molecule only upon removal of the molecular moiety.

Another aspect of the disclosure provides an oligonucleotide comprising about 6 to 60 nucleotides. The 3' end the oligonucleotide can have a molecular moiety that is non-binding with respect to a target nucleic acid molecule; is recognizable by a polymerase having 3' to 5' exonuclease activity; and is cleavable by the 3' to 5' exonuclease activity of the polymerase during amplification of the target nucleic acid molecule.

An additional aspect of the disclosure provides a primer set that can comprise a forward primer and reverse primer. Each of the forward and reverse primers, from a 5' end to 3' end, can comprise a nucleotide sequence A that is substantially complementary to a target nucleic acid molecule or a complement thereof; and a molecular moiety at its 3' end that is non-complementary with respect to one or more corresponding nucleotides of the target nucleic acid molecule or the complement thereof. Moreover, the molecular moiety of the forward primer and the molecular moiety of the reverse primer can be non-complementary to each other and the forward and reverse primers can be extendable in a template-directed manner only upon removal of the molecular moiety.

In some aspects, a primer or oligonucleotide described herein may be included in a primer or oligonucleotide set. The primer or oligonucleotide set can comprise at least one additional primer or oligonucleotide that exhibits sequence complementarity to a complement nucleic acid strand of the target nucleic acid molecule. In some embodiments, a primer set or oligonucleotide set described herein, when used in an amplification reaction in the presence of a polymerase that has 3' to 5' exonuclease activity and/or an enzyme that has endonuclease activity, can yield amplified target nucleic acids that are substantially free from primer dimer by-products or oligonucleotide dimer by-products. As used herein, "substantially free from primer dimer by-products or oligonucleotide dimer by-products" generally refers to a concentration of primer dimer by-products or oligonucleotide by-products of less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.1%, 0.01%, 0.001%, or less of amplified nucleic acid product(s) as measured by a melting curve analysis (or other suitable analysis such as, for example, gel electrophoresis) of the amplified nucleic acid product(s).

Additionally, a primer, oligonucleotide, primer set or oligonucleotide set described herein may be included in a solution. Such a solution may be, for example, an amplification reaction mixture (as described elsewhere herein) that comprises one or more reagents necessary for amplification of a nucleic acid molecule. In some embodiments, the solution may comprise one or more reagents necessary for amplification of a nucleic acid molecule such that when the solution is mixed with one or more additional solutions, an amplification reaction mixture is obtained. Additional examples of solutions that can include a primer, oligonucleotide, primer set or oligonucleotide set include water, a buffer, a solvent, a biological fluid (e.g., blood), a fluid containing a solid biological sample (e.g., animal tissue, plant sample, etc.).

Moreover, a primer (including a primer of a primer set) or an oligonucleotide (including an oligonucleotide of an oligonucleotide set) described herein may be an isolated and purified nucleic acid strand. An isolated and purified nucleic acid strand generally refers to a nucleic acid strand that is free or substantially free of other species, including other nucleic acids. In some embodiments, a primer (including a primer of a primer set) or an oligonucleotide (including an oligonucleotide of an oligonucleotide set) may be synthetic. In addition, in some embodiments, the 3' end of a primer (including a primer of a primer set) or an oligonucleotide (including an oligonucleotide of an oligonucleotide set) described herein may be recognizable and/or cleavable by an enzyme (e.g., a polymerase) that has 3' to 5' exonuclease activity. In some embodiments, the 3' end of a primer (including a primer of a primer set) or oligonucleotide (or an oligonucleotide set) described herein may be recognizable and/or cleavable by an enzyme (e.g., a polymerase) with endonuclease activity. In some embodiments, the 3' end of a primer or oligonucleotide described herein may be recognizable and/or cleavable by both an enzyme with 3' to 5' exonuclease activity and an enzyme with endonuclease activity. In some embodiments, the 3' end of a primer or oligonucleotide described herein may be recognizable and/or cleavable by an enzyme with both 3' to 5' exonuclease activity and endonuclease activity.

The length of a primer (including a primer of a primer set) oligonucleotide (including an oligonucleotide of an oligonucleotide set) described herein may vary depending upon the particular primer or oligonucleotide and/or application in which the primer or oligonucleotide is used. For example, the length of primer or oligonucleotide described herein may be from about 3 nucleotides to about 70 nucleotides. In some embodiments, the length of primer or oligonucleotide described herein may be from about 6 nucleotides to about 60 nucleotides. In some embodiments, the length of primer or oligonucleotide described herein may be from about 10 nucleotides to about 60 nucleotides. In some embodiments, the length of primer or oligonucleotide described herein may be from about 6 nucleotides to about 50 nucleotides. In some embodiments, the length of primer or oligonucleotide described herein may be from about 6 nucleotides to about 40 nucleotides. In some embodiments, the length of primer or oligonucleotide described herein may be from about 6 nucleotides to about 30 nucleotides. In some embodiments, the length of primer or oligonucleotide described herein may be from about 6 nucleotides to about 20 nucleotides. In some embodiments, the length of primer or oligonucleotide described herein may be from about 6 nucleotides to about 10 nucleotides. In some embodiments, the length of primer or oligonucleotide described herein may be from about 11 nucleotides to about 30 nucleotides. In some embodiments, the length of primer or oligonucleotide described herein may be from about 10 nucleotides to about 20 nucleotides. In some embodiments, the length of a primer or oligonucleotide described herein may be about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides.

Additionally, a primer (including a primer of a primer set) described herein may comprise a nucleotide sequence A that is complementary or substantially complementary to a target nucleic acid molecule. Similarly, an oligonucleotide (including an oligonucleotide of an oligonucleotide set) described herein may also comprise a nucleotide sequence A that is complementary or substantially complementary to a target nucleic molecule. Such a nucleotide sequence A can exhibit sequence complementarity to itself and/or a molecular moiety. In some embodiments, a primer or oligonucleotide described herein may be a hairpin loop primer characterized in that its nucleotide sequence A exhibits sequence complementarity to itself and/or a molecular moiety.

The length of a nucleotide sequence A of a primer (including a primer of a primer set) or oligonucleotide (including an oligonucleotide of an oligonucleotide set) described herein may vary depending upon the particular primer or oligonucleotide. For example, the length of a nucleotide sequence A of a primer or oligonucleotide described herein may be from about 6 nucleotides to about 60 nucleotides. In some embodiments, the length of a nucleotide sequence A of a primer or oligonucleotide described herein may be about 6 nucleotides to about 50 nucleotides. In some embodiments, the length of a nucleotide sequence A of a primer or oligonucleotide described herein may be about 6 nucleotides to about 40 nucleotides. In some embodiments, the length of a nucleotide sequence A of a primer or oligonucleotide described herein may be about 6 nucleotides to about 30 nucleotides. In some embodiments, the length of a nucleotide sequence A of a primer or oligonucleotide described herein may be about 6 nucleotides to about 22 nucleotides. In some embodiments, the length of a nucleotide sequence A of a primer or oligonucleotide sequence described herein may be about 6 nucleotides to about 20 nucleotides. In some embodiments, the length of a nucleotide sequence A of a primer or oligonucleotide sequence described herein may be about 6 nucleotides to about 10 nucleotides. In some embodiments, the length of a primer or oligonucleotide described herein may be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 nucleotides or may be longer or shorter. Additionally, a nucleotide sequence A of a primer or oligonucleotide described herein may be of a length that provides sufficient complementarity with respect to a target nucleic acid molecule. Sufficient complementarity of a nucleotide sequence A can help in controlling the melting temperature of the nucleotide sequence A.

A primer (including a primer of a primer set) or oligonucleotide (including an oligonucleotide of an oligonucleotide set) described herein may comprise a molecular moiety at its 3' end that is non-complementary and/or non-binding with respect to a target nucleic acid molecule. In some embodiments, a molecular moiety of a primer or oligonucleotide described herein may be adapted to prevent the formation of a primer dimer by-product that comprises the primer (e.g., a forward primer) or an oligonucleotide dimer by-product that comprises the oligonucleotide. For example, the presence of a molecular moiety in a primer or oligonucleotide described herein may reduce the binding affinity (or prevent binding) of the primer or oligonucleotide for an additional primer or oligonucleotide. The presence of a molecular moiety may also reduce or eliminate the possibility that the primer or oligonucleotide can be extended in an amplification reaction, using, for example, another primer or oligonucleotide as a template. Upon removal of the molecular moiety, the primer or oligonucleotide can then be extended. In the case of a primer set comprising a forward primer and a reverse primer each comprising a molecular moiety, one or both of the molecular moieties may be adapted to prevent the formation of a primer dimer molecular complex comprising the forward primer and/or reverse primer.

A molecular moiety may be any suitable species. In some embodiments, a molecular moiety may comprise one or more phosphodiester bonds. Non-limiting examples of molecular moieties include nucleotides, nucleic acids and non-nucleotide species (e.g., amino acids, peptides, proteins, carbohydrates, hydrocarbon chains (e.g., polyethylene glycol (PEG)), an n-phosphate moiety (where "n" is greater than or equal to 1, 2, 3, 4, 5, 6, 7, 8, 9, or 10), phosphodiester bond linked hetero-conjugates, dyes and organic-metal complexes). Moreover, a molecular moiety may also comprise individual subunits or species linked together (either continuously or discontinuously) via covalent bonds. Such individual species or subunits may be, for example, one or more individual nucleotides of a nucleic acid, one or more amino acids of a peptide or protein, or one or more sugars of a carbohydrate. For example, the length of a molecular moiety may be about 1 to 20, 1 to 15, 1 to 10 or 1 to 5 individual specie or subunits. In some embodiments, the length of a molecular moiety may be about 1, 2, 3, 4, 5, 6, 7, 8, 9, 10, 11, 12, 13, 14, 15 or more individual species or subunits. In some embodiments, the length of a molecular moiety can be useful in modulating the rate of a nucleic acid amplification reaction in which the molecular moiety participates.

In some embodiments, a molecular moiety of a primer or oligonucleotide described herein may comprise a nucleic acid. A molecular moiety of a primer or oligonucleotide described herein that comprises nucleic acid may reduce (or prevent) the ability of the primer or oligonucleotide to hybridize with another primer or oligonucleotide and or be extended in an amplification reaction. In some embodiments, the molecular moieties of a forward primer and reverse primer in a primer set may not be complementary to each other, such that the lack of sequence complementarity between the molecular moieties reduces (or prevents) the ability of the forward and reverse primers to hybridize to each other during an amplification reaction. In some embodiments, a molecular moiety can be linked to a primer or oligonucleotide via one or more phosphodiester bonds that can be separated by ribose or deoxyribose and/or the molecular moiety can be terminated with a hydroxyl group.

In addition, a molecular moiety of a primer or oligonucleotide described herein may be adapted such that its melting temperature is lower than the melting temperature of a portion of a nucleotide sequence of the primer or oligonucleotide. A lower melting temperature of a molecular moiety may reduce the likelihood (or prevent) binding of the molecular moiety to a target nucleic acid molecule at a primer or oligonucleotide annealing temperature that is higher than the melting temperature of the molecular moiety.

Accordingly, the molecular moiety may comprise at least one, two, three, four, five, six, seven, eight, nine, ten or more nucleotides or nucleotide analogues. In some embodiments, a molecular moiety may comprise one or more nucleotide analogues having an unnatural base. Non-limiting examples of nucleotide analogues having an unnatural base include inosine (including a base of hypoxanthine), uracil-containing nucleotides (in cases where a nucleic acid is DNA), iso-dC, iso-dG, diaminopurine, 2,4-difluorotoluene, 4-methylbenzimidazole, size-expanded xA, size-expanded xG, size-expanded xC, size-expanded xT, d5SICS and dNaM. In some embodiments, a molecular moiety may comprise one or more nucleotide analogues that have no base (e.g., abasic nucleotides, acyclo nucleotides). In some embodiments, a molecular moiety may comprise a terminator nucleotide that cannot be extended by a polymerase without removal (e.g., via an enzyme with proofreading activity, such as an exonuclease or endonuclease).

Moreover, the length of a molecular moiety that comprises nucleic acid may vary. For example, the length of a molecular moiety that comprises nucleic acid may be about 1, 2, 3, 4, 5, 6, 7, 8, 9, 10, 11, 12, 13, 14, 15 or more nucleotides or nucleotide analogues. In embodiments where a primer (including a primer of a primer set) or oligonucleotide (including an oligonucleotide of an oligonucleotide set) described here comprises a nucleotide sequence A that is complementary or substantially complementary to a target nucleic acid (including cases where nucleotide sequence A exhibits sequence complementarity to itself and/or a molecular moiety), a molecular moiety of the primer or oligonucleotide may comprise a nucleotide sequence B having 1-15, 1-10, 1-8, 1-6, or 1-4 consecutive nucleotides that are non-complementary with respect to 1-15, 1-10, 1-8, 1-6 or 1-4 corresponding nucleotides of a target nucleic acid molecule.

Moreover, a molecular moiety of a primer or oligonucleotide can be a substrate of an exonuclease, an endonuclease or both types of enzymes. Examples of exonucleases and endonucleases are described elsewhere herein. In such cases, an appropriate exonuclease and/or endonuclease can be used to remove the molecular moiety.

Additionally, in some embodiments, a primer or oligonucleotide described herein may comprise at least one, two, three, four, five, six, seven, eight, nine, ten, eleven, twelve, thirteen, fourteen, fifteen or more "stopper" or "blocker" nucleotides that can be nuclease (e.g., exonuclease, endonuclease) resistant and/or exert resistance to an enzyme with proofreading activity (e.g., an enzyme having 3' to 5' exonuclease activity). Such a stopper or blocker nucleotide can be positioned at the 3' end of a primer or oligonucleotide and may slow down or prevent further action of a nuclease and/or an enzyme with proofreading activity (e.g., an enzyme having 3' to 5' exonuclease activity). In embodiments where the primer or oligonucleotide also comprises a molecular moiety, the stopper or blocker nucleotide(s) can be positioned adjacent to the molecular moiety in order to permit removal of the molecular moiety but minimize or prevent further removal additional primer nucleotides 5' of the molecular moiety. Upon inhibition or slowing down of the activity of such a nuclease and/or enzyme having proofreading activity, a polymerase can then extend the 3' region of the primer or oligonucleotide. A stopper or blocker nucleotide and the number of such nucleotides in a molecular moiety may also be used to control primer length, annealing times, denaturation times, extension initiation times, extension times, and number of cycles needed for nucleic acid amplification as described elsewhere herein. A stopper or blocker can be a nuclease (e.g., exonuclease, endonuclease) resistant species. Non-limiting examples of such species include nuclease resistant nucleotides, phosphothioate, locked nucleic acids (LNAs), bridged nucleic acids (BNAs), fluorinated nucleic acids (FNAs) and alpha-thio nucleotides.

Figure 11A:
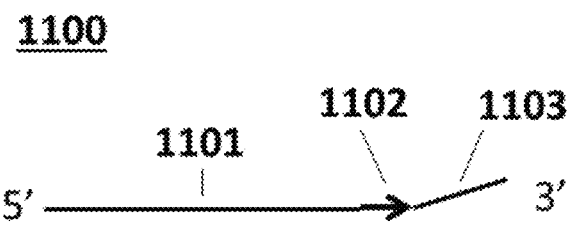
FIG. 11A is schematic depicting an example primer comprising a stopper or blocker region.

An example primer 1100 comprising a priming region 1101 (e.g., comprising a nucleotide sequence A), a stopper or blocker region 1102 comprising one or more stopper or blocker nucleotides and a molecular moiety 1103 (e.g., comprising a nucleotide sequence B) is shown in FIG. 11A. The priming region 1101 is 5' to the stopper or blocker region 1102 which is 5' to the molecular moiety 1103. The molecular moiety 1103 can be removed via the action of an enzyme having 3' to 5' exonuclease activity. As an enzyme with 3' to 5' exonuclease activity comes into contact with a stopper or blocker nucleotides in the stopper or blocker region 1102, the activity of the enzyme is either completely inhibited or impeded such that the "proofreading" activity of such an enzyme stops or becomes slower.

Moreover, a primer (including a primer of a primer set) or an oligonucleotide (including an oligonucleotide of an oligonucleotide set) described herein may be adapted for use in any suitable type of nucleic acid amplification reaction, including example types of nucleic acid amplification reactions and methods described elsewhere herein. For example, a primer or an oligonucleotide described herein may be adapted for use in a reverse transcription polymerase chain reaction (RT-PCR), as described elsewhere herein.

In addition, a primer (including a primer of a primer set) or an oligonucleotide (including an oligonucleotide of an oligonucleotide set) described herein may be suitable for use in single nucleotide polymorphism detection including example methods of single nucleotide polymorphism detection described elsewhere herein. As used herein, "single nucleotide polymorphism detection" generally refers to the detection of single nucleotide polymorphisms (SNPs), a type of sequence-level genetic variation in a population of living subjects. In some embodiments, a primer or oligonucleotide may comprise nucleotides with unnatural bases (e.g., hypoxanthine of inosine, uracil-containing nucleotides) in its molecular moiety. Such unnatural bases may be used to interrogate particular SNP sites as described elsewhere herein.

Additional applications in which a primer (including a primer of a primer set) or an oligonucleotide (including an oligonucleotide of an oligonucleotide set) described herein may be suitable include genotyping detection, mutation detection, gene expression detection, low quantity nucleic acid detection, viral stain/subtype detection, bacterial drug resistance detection and transgenic organism detection.

Additional aspects of the disclosure provide methods for nucleic acid amplification. In general, methods for nucleic acid amplification described herein rely on primers that comprise molecular moieties at their 3' ends that are removed or cleaved (e.g., via the action of enzyme with proofreading activity) prior to primer extension in a nucleic acid amplification reaction. An example method for nucleic acid amplification is schematically depicted in FIG. 1. As shown in FIG. 1, a forward primer 101 and a reverse primer 102 anneal to their respective strands of a double-stranded target nucleic acid molecule 105. The forward primer 101 and reverse primer 102 comprise molecular moieties 103 and 104, respectively, at their 3' ends. Molecular moieties 103 and 104 are cleaved or removed (e.g., via the action of one or more enzymes comprising proofreading activity such as an enzyme with 3' to 5' exonuclease activity, an enzyme with endonuclease activity, or both types of enzymes) 106 to render the 3' ends of forward primer 101 and reverse primer 102 extendable in a primer extension reaction. The primers are then extended 107 in a primer extension reaction to generate double-stranded amplification products 108a and 108b.

In one aspect, the disclosure provides a method for nucleic acid amplification. The method can comprise annealing a forward primer to a single-stranded target nucleic acid molecule and a reverse primer to a complement of the single-stranded target nucleic acid molecule; extending the forward primer and reverse primer in a template-directed manner to yield double-stranded target nucleic acid molecules; denaturing the double-stranded target nucleic acid molecules to generate single-stranded target nucleic acid molecules; and repeating annealing, extending and denaturing of the forward and reverse primers for at least one cycle to yield amplified double-stranded target nucleic acid molecules. Each of the forward and reverse primers, from a 5' end to 3' end, can comprise a molecular moiety at a 3' end that is non-complementary with respect to one or more corresponding nucleotides of the single-stranded target nucleic acid molecule or the complement. Moreover, the molecular moieties of the forward primer and reverse primers may or may not be complementary to each other.

In some embodiments, after repeating annealing, extending and denaturing of the forward and reverse primers for at least one cycle, primer dimer by-products comprising the forward primer and/or the reverse primer may be present at a concentration that is less than about 30%, 29%, 28%, 27%, 26%, 25%, 24%, 23%, 22%, 21%, 22%, 20%, 19%, 18%, 17%, 16%, 15%, 14%, 13%, 12%, 11%, 10%, 9%, 8%, 7%, 6%, 5%, 4%, 3%, 2%, 1%, 0.1%, 0.01% or less of the amplified double-stranded target nucleic acid molecules as measured by a melting curve analysis (or other suitable method of analysis, such as, for example gel electrophoresis) of the amplified double-stranded target nucleic acid molecules. In some embodiments, the method can further comprise, prior to extending the forward and reverse primers, removing the molecular moieties of the forward and reverse primers using any suitable removal method including example removal methods described elsewhere herein.

In another aspect, the disclosure provides a method for nucleic acid amplification. The method can comprise subjecting a reaction mixture containing a nucleic acid sample having a single-stranded target nucleic acid molecule to a nucleic acid amplification reaction under conditions to yield an amplified product of the nucleic acid sample. The reaction mixture can comprise a forward primer that is complementary to the single-stranded target nucleic acid molecule and comprises a first molecular moiety at a 3' end that is non-complementary with respect to one or more corresponding nucleotides of the single-stranded target nucleic acid molecule. The reaction mixture can also comprise a reverse primer that is complementary to a complement of the single-stranded target nucleic acid molecule and comprises a second molecular moiety at a 3' end that is non-complementary with respect to one or more corresponding nucleotides of the complement. The first molecular moiety and the second molecular moiety may or may not be complementary to each other.

In some embodiments, subjecting the reaction mixture to the nucleic acid amplification reaction may comprise extending the forward and reverse primers in a template-directed manner to yield double-stranded target nucleic acid molecules. The first and second molecular moieties of the forward and reverse primers, respectively, may be removed prior to extending the forward and reverse primers using any suitable removal method including example removal methods described elsewhere herein. For example, the first and second molecular moieties may be removable with the aid of the 3' to 5' exonuclease activity of a polymerase in the reaction mixture.

In another aspect, the disclosure provides a method for nucleic acid amplification. The method can comprise providing a reaction mixture comprising a forward primer complementary to a target nucleic acid molecule, a reverse primer complementary to a complement of the target nucleic acid molecule and the target nucleic acid molecule. The method further comprises using the forward primer and the reverse primer to perform multiple amplification cycles to generate amplified products of the target nucleic acid molecule in the reaction mixture. After 20 or more amplification cycles, a concentration of a primer dimer molecular complex comprising a sequence of the forward and/or a sequence of the reverse primer in the reaction mixture can be less than about 10% of the amplified products of the target nucleic acid molecule as measured by a melting curve analysis (or other suitable method of analysis, such as, for example gel electrophoresis) of the amplified products of the target nucleic acid molecule.

In various aspects, the forward and reverse primers used in methods for nucleic acid amplification described herein may have any suitable characteristics or properties of a primer including any of the various characteristics and properties of primers described elsewhere herein. The forward and reverse primers can comprise any suitable primer including any of the various primers described elsewhere herein. Moreover, a molecular moiety of a forward primer and a molecular moiety of a reverse primer used in a method for nucleic acid amplification described herein may have any suitable characteristics or properties of a molecular moiety including any of the various characteristics and properties of molecular moieties described elsewhere herein. For example, a forward and reverse primer each comprising molecular moieties and used in a method for nucleic acid amplification described herein may be adapted to prevent the formation of a primer dimer molecule complex comprising the forward primer and/or reverse primer. The molecular moieties of the forward and reverse primers used in methods for nucleic acid amplification described herein may comprise any suitable molecular moiety including the various molecular moieties described elsewhere herein. Furthermore, the forward and reverse primers used in methods for nucleic acid amplification described herein may be included in a primer set including any of the primer sets described elsewhere herein.

As described with respect to primers described elsewhere herein, a forward primer and/or reverse primer used in a method for nucleic acid amplification described herein may comprise a molecular moiety. In some embodiments, a forward primer used in a method for nucleic acid amplification described herein may comprise a molecular moiety at a 3' end that is non-complementary with respect to a target nucleic acid molecule and/or a reverse primer used in a method for nucleic acid amplification described herein may comprise a molecular moiety at a 3' end that is non-complementary with respect to a complement of a target nucleic acid molecule. Prior to extension of a forward and/or reverse primer to yield a double-stranded nucleic acid molecule (e.g., a double-stranded target nucleic acid molecule), a molecular moiety of a forward and/or reverse primer may be removed prior to extension proceeding. Moreover, a molecular moiety may be cleavable or removable from a forward and/or reverse primer. Removal or cleavage of a molecular moiety from a forward and/or reverse primer may be completed via any suitable method. In some embodiments, a molecular moiety of forward and/or reverse primer can be removed chemically and/or physically. In some embodiments, removal of a molecular moiety from its primer or oligonucleotide can occur while the primer or oligonucleotide is hybridized with its complementary sequence on a target nucleic acid molecule.

In some embodiments, removal or cleavage of a molecular moiety may be completed via the action of an enzyme (e.g., polymerase) with 3' to 5' exonuclease activity. Such an enzyme may "proofread" the molecular moiety such that individual species or subunits (e.g., non-complementary nucleotides) of the molecular moiety are removed one-by-one from the associated primer at its 3' end in sequential fashion by the enzyme with 3' to 5' exonuclease activity. Any suitable enzyme with 3' to 5' activity may be used to remove or cleave a molecular moiety from a forward and/or reverse primer. Non-limiting examples of enzymes with 3' to 5' exonuclease activity include naturally occurring exonucleases, engineered exonucleases, Phusion polymerase, Pfu polymerase, DEEPVENT polymerase, exonuclease I, exonuclease III, exonuclease IV, exonuclease V, KOD polymerase, Q5 DNA polymerase, Advantage HD polymerase, PrimeSTAR GXL DNA polymerase, Bst polymerase and Phi29 DNA polymerase.

In some embodiments, removal of a molecular moiety from a forward and/or reverse primer may be completed via the action of an enzyme (e.g., polymerase) with endonuclease activity. Such an enzyme may "proofread" the molecular moiety such that the entire molecular moiety is removed as a single species via, for example, the cleavage of a phosphodiester bond linking the molecular moiety to a primer. Any suitable enzyme with endonuclease activity may be used to remove or cleave a molecular moiety from a forward and/or reverse primer. Non-limiting examples of enzymes with endonuclease activity include naturally occurring endonucleases, engineered endonucleases, deoxyribonuclease I, Type I restriction endonucleases, Type II restriction endonucleases, Type III restriction endonucleases, thermal stable RNase HII, thermal stable RNase H1 and thermal stable uracil DNA-glycosylase (UDG).

As described with respect to primers described elsewhere herein, a forward primer and/or reverse primer used in a method for nucleic acid amplification described herein may comprise one or more stopper or blocker nucleotides. Such stopper or blocker nucleotides may have any suitable characteristics or properties of stopper or blocker nucleotides including any of the various characteristics and properties of stopper or blocker nucleotides described elsewhere herein. Moreover, stopper or blocker nucleotides of the forward and/or reverse primers used in methods for nucleic acid amplification described herein may be configured in any suitable for configuration. For example, a forward and/or reverse primer used in a method for nucleic acid amplification described herein may be configured in similar fashion to the example primer depicted in FIG. 11A.

Figure 11B:
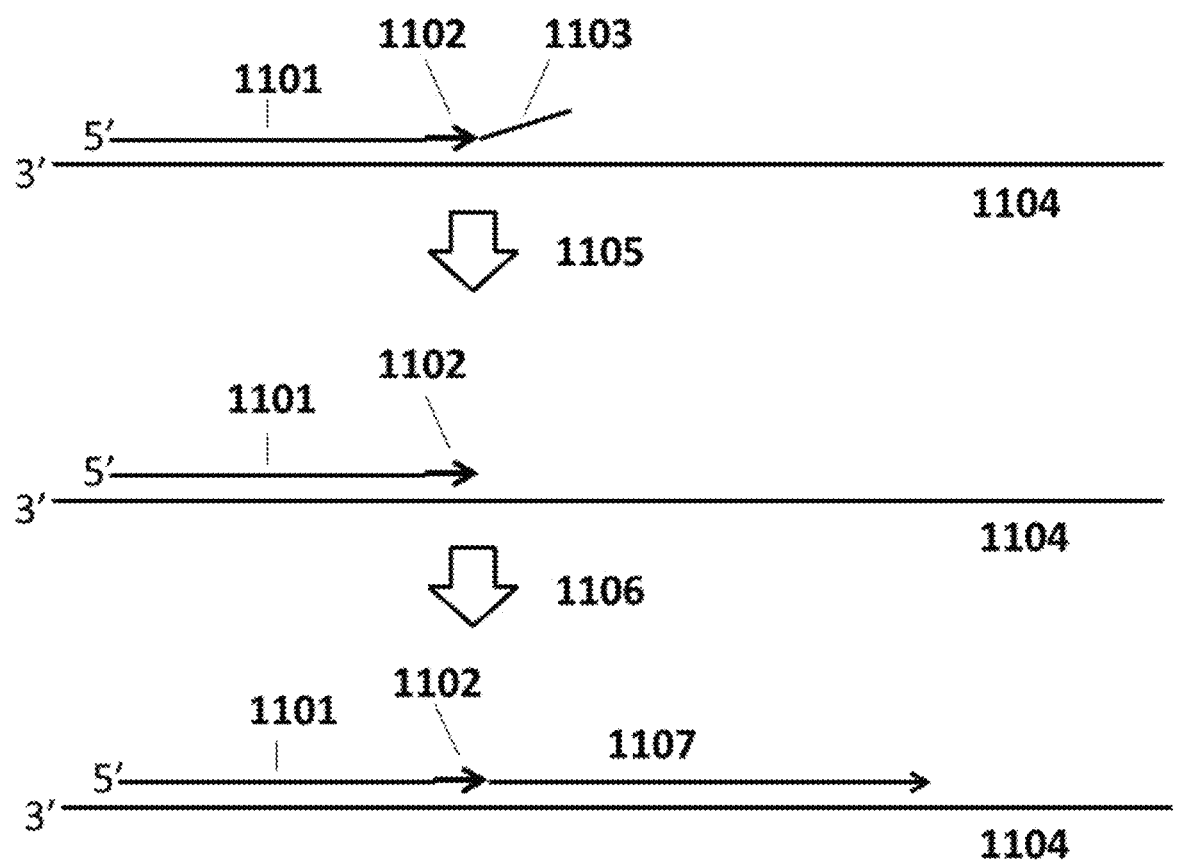
FIG. 11B is schematic depicting an example method for nucleic acid amplification using an example primer comprising a stopper or blocker region.

An example method for nucleic acid amplification utilizing a forward primer with a stopper or blocker region is schematically depicted in FIG. 11B. As shown in FIG. 11B, a forward primer similar to the example primer shown in FIG. 11A comprises, 5' to 3' a priming region 1101 (e.g., a nucleotide sequence A), a stopper or blocker region 1102 and a molecular moiety 1103. The molecular moiety 1103 can be removed from the forward primer via action of an enzyme having 3' to 5' exonuclease activity. Moreover, the stopper or blocker region 1102 comprises one or more stopper or blocker oligonucleotides. The forward primer hybridizes with its complementary sequence on a target nucleic acid molecule 1104. Upon hybridization, the activity 1105 of an enzyme having 3' to 5' exonuclease removes the molecular moiety 1103 from the forward primer. The presence of the one or more stopper or blocker oligonucleotides prevents the enzyme having the 3' to 5' exonuclease activity from further "proofreading" activity once it reaches the stopper or blocker region 1102. The activity 1106 of a polymerase can then extend 1107 the forward primer at its 3' end (e.g., 3' to the stopper or blocker region 1102). Extension generates a double-stranded nucleic acid product which can then participate in additional rounds of nucleic acid amplification. In some embodiments, the enzyme having the 3' to 5' exonuclease activity 1105 and the enzyme having the polymerase activity 1106 are different enzymes. In some embodiments, the enzyme having the 3' to 5' exonuclease activity 1105 and the enzyme having the polymerase activity 1106 are the same enzyme.

Methods for nucleic acid described herein may be useful in minimizing or preventing the generation of primer dimer by-products or primer dimer molecular complexes as described elsewhere herein. Using a forward primer and/or reverse primer in a method for nucleic acid amplification described herein, amplified products of a target nucleic acid molecule or amplified products of a double-stranded target nucleic acid molecule may be generated after multiple amplification cycles. In some embodiments, after 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amplification cycles, the concentration of a primer dimer molecule complex comprising a sequence of a forward primer and/or a sequence of a reverse primer in an amplification reaction mixture may be less than about 30%, 29%, 28%, 27%, 26%, 25%, 24%, 23%, 22%, 21%, 22%, 20%, 19%, 18%, 17%, 16%, 15%, 14%, 13%, 12%, 11%, 10%, 9%, 8%, 7%, 6%, 5%, 4%, 3%, 2%, 1%, 0.1%, 0.01% or less of the amplified products of the target nucleic molecule, as determined by any suitable analysis of the amplified products, such as, for example, melting curve analysis or gel electrophoresis of the amplified products as described elsewhere herein. In some embodiments, a primer dimer molecular complex or by-product may be undetectable by a detection method (e.g., melting curve analysis or gel electrophoresis) in a reaction mixture after completing a method for nucleic acid amplification described herein.

In general, nucleic acid amplification may occur in a reaction mixture in which the nucleic acid molecule to be amplified is provided along with any additional reagents (e.g., one or more of forward primers, reverse primers, polymerases, exonuclease, endonuclease, dNTPs, co-factors, suitable buffers, etc.) necessary for amplification of the nucleic acid molecule. Other reagents (e.g., a detectable species such as a probe or dye) may also be included in a reaction mixture that may be useful for the detection of an amplification product The reaction mixture may then be subjected to conditions (e.g., appropriate temperatures, addition/removal of heat, buffer concentrations, etc.) suitable for amplifying the nucleic acid molecule. For example, a single or double-stranded target nucleic acid molecule may be provided in a reaction mixture that also comprises any additional reagents (e.g., one or more of a forward primers and reverse primers described elsewhere herein, a polymerase, an exonuclease, an endonuclease, dNTPs, co-factors, buffers, other enzymes (e.g., a reverse transcriptase to generate cDNA from RNA, a ligase, etc.) necessary for amplification of the single or double-stranded target nucleic acid molecule. In some embodiments, the temperature of the reaction mixture may be cycled repeatedly through a denaturation temperature (e.g., to denature, separate or melt double-stranded nucleic acid molecules into component nucleic acid strands), an annealing temperature (e.g., to anneal or hybridize a primer to each of the component nucleic acid strands) and an extension temperature (e.g., to extend or add nucleotides to the annealed primers in a primer extension reaction via the action of a polymerase) in order to amplify the single-stranded or double-stranded target nucleic acid molecule.

The cycling of the temperature of a reaction mixture may be achieved, for example, with the aid of any suitable thermocycler instrument or other type of device capable of cyclical heating. Such an instrument may include or may be coupled to a device suitable of detecting amplification products in a reaction mixture, as described elsewhere herein. In some embodiments, such a device may be capable of optically detecting an optically-responsive species in a reaction mixture, where such optical detection can be used for quantification of amplification products, measurement of Ct values, and/or melting point detection. In some embodiments, detection of amplified products can be performed in real-time (e.g., as the amplification reaction proceeds). In some embodiments, denaturation of a double-stranded nucleic acid molecule may be achieved via a denaturing agent, such as, for example an alkaline agent (e.g. sodium hydroxide (NaOH)).

In some cases, amplification of a nucleic acid may be achieved isothermally such as, for example, without a change in temperature of a reaction mixture. In some embodiments, a method for nucleic acid amplification described herein may be completed without cycling the temperature of an amplification reaction mixture. For example, multiple amplification cycles may be performed without cycling the temperature of a reaction mixture.

In some embodiments, a reaction mixture may be heated to one or more reaction temperatures via the aid of a thermal gradient. The thermal gradient may, for example, be generated by one or more isothermal heating sources or one or more fixed heating sources. For example, a reaction mixture may be heated in a convection-based thermal gradient instrument such as, for example, via Rayleigh-Bernard convection. Such an instrument may include or may be coupled to a device suitable of detecting amplification products in a reaction mixture, as described elsewhere herein. In some embodiments, such a device may be capable of optically detecting an optically-responsive species in a reaction mixture, where such optical detection can be used for quantification of amplification products, measurement of Ct values, and/or melting point detection. In some embodiments, detection of amplified products via convection-based strategies and/or instruments can be performed in real-time (e.g., as the amplification reaction proceeds), including detection via detection of melting points.

An example of a convection-based strategy and system include the iiPCR method used in a POCKIT system. Such a system can include a single heating source at the bottom of one or more vessels (e.g., capillary tubes) that drives an amplification reaction via Rayleigh-Bernard convection. When Rayleigh-Bernard convection is used to drive an amplification reaction, the temperature changes of different "parts" of the reaction mixture are generally not synchronized. In such cases, different parts of a reaction mixture in a reaction vessel can have different temperatures. Such temperature differences can be as large as 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C. or more. Moreover, a region of the reaction mixture can be moved to different regions of the reaction vessel due to temperature-related density differences among different regions.

An additional feature of Rayleigh-Bernard convection based amplification is that each given part of a reaction mixture can undergo continuous temperature changes along a temperature gradient that is generated by one or more isothermal heating sources. Such temperature changes can permit amplification of a nucleic acid molecule using an isothermal heating source.

Any step of a method for nucleic acid amplification described herein may be performed in a partition. In some embodiments, all steps of a method for nucleic acid described herein may be performed in a partition. In some embodiments, a reaction mixture in which nucleic acid amplification takes place may be in a partition. A partition used in a method for nucleic acid amplification described herein may be any suitable type of partition with non-limiting examples of partitions that include a droplet (e.g., a droplet in an emulsion, such as, for example, a water-in-oil emulsion or oil-in-water emulsion), a well (e.g., a well among an array of wells such as a well in a microwell plate), a microwell (e.g., a microwell on a flat substrate), a patterned well and a vessel (e.g., any suitable type of tube, a capillary tube, a centrifuge tube, a cuvette, a pipette tip, a bag, a box, a container). In embodiments where a partition is a well, the well walls (surfaces) can be made of hydrophilic materials that can aid in retaining an aqueous reaction mixture within the wells. In some embodiments, a well is a micro-fabricated or patterned microwell in an array of microwells of a flat substrate. The flat substrate can be coated with polyethylene glycol (PEG) or a hydrophobic material so that an oil phase can be applied over aqueous materials (e.g., droplets) within the micro-wells (e.g., "half-emulsions"). Moreover, in cases where a partition is a droplet, the droplet may be generated by bulk emulsification methods and/or with the aid of a microfluidic device. Bulk emulsification and/or microfluidic devices may also be useful in partitioning species into droplets.

A nucleic acid amplification reaction can include the use and action of a polymerase. During a primer extension reaction, a polymerase can generally add, in template-directed fashion, nucleotides to the 3' end of a primer annealed to a single-stranded nucleic acid molecule. Any suitable polymerase may be used for a primer extension reaction, including commercially available polymerases. Non-limiting examples of polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, Phusion polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, Q5 DNA polymerase, Advantage HD Polymerase, PrimeSTAR GXL DNA polymerase, polymerase with 3' to 5' exonuclease activity, and variants, modified products and derivatives thereof.

In some embodiments, a suitable denaturation temperature may be, for example, about 60° C., 61° C., 62° C., 63° C., 64° C., 65° C., 66° C., 67° C., 68° C., 69° C., 70° C., 71° C., 72° C. 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 93° C., 94° C., 95° C., 96° C., 97° C., 98° C., 99° C., 100° C., 101° C., 102° C., 103° C., 104° C., 105° C. or higher. In some embodiments, a suitable denaturation time for a single amplification cycle may be, for example, about 0.1 seconds ("s"), 0.5 s, 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, 21 s, 22 s, 23 s, 24 s, 25 s, 26 s, 27 s, 28 s, 29 s, 30 s, 31 s, 32 s, 33 s, 34 s, 35 s, 36 s, 37 s, 38 s, 39 s, 40 s, 41 s, 42 s, 43 s, 44 s, 45 s, 46 s, 47 s, 48 s, 49 s, 50 s, 51 s, 52 s, 53 s, 54 s, 55 s, 56 s, 57 s, 58 s, 59 s, 1 minute, 2 minutes, 3 minutes, 4 minutes, 5 minutes or longer.

In some embodiments, a suitable annealing temperature may be, for example, about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher. In some embodiments, a suitable annealing time for a single amplification cycle may be, for example, about 0.1 s, 0.5 s, 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, 21 s, 22 s, 23 s, 24 s, 25 s, 26 s, 27 s, 28 s, 29 s, 30 s, 31 s, 32 s, 33 s, 34 s, 35 s, 36 s, 37 s, 38 s, 39 s, 40 s, 41 s, 42 s, 43 s, 44 s, 45 s, 46 s, 47 s, 48 s, 49 s, 50 s, 51 s, 52 s, 53 s, 54 s, 55 s, 56 s, 57 s, 58 s, 59 s, 1 minute, 2 minutes, 3 minutes, 4 minutes, 5 minutes or longer.

In some embodiments, a suitable extension temperature may be, for example, about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., or higher. In some embodiments, a suitable extension temperature may be the same temperature as a suitable annealing temperature. In some embodiments, a suitable extension time for a single amplification cycle may be, for example, about 0.1 s, 0.5 s, 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, 21 s, 22 s, 23 s, 24 s, 25 s, 26 s, 27 s, 28 s, 29 s, 30 s, 31 s, 32 s, 33 s, 34 s, 35 s, 36 s, 37 s, 38 s, 39 s, 40 s, 41 s, 42 s, 43 s, 44 s, 45 s, 46 s, 47 s, 48 s, 49 s, 50 s, 51 s, 52 s, 53 s, 54 s, 55 s, 56 s, 57 s, 58 s, 59 s, 1 minute, 2 minutes, 3 minutes, 4 minutes, 5 minutes or longer.

Any suitable type of nucleic acid amplification reaction may be used to amplify a nucleic acid molecule. One example of a nucleic acid amplification reaction is a polymerase chain reaction (PCR) that relies on repeated cycles of primer annealing, primer extension and denaturing of amplified nucleic acid molecules as described above. Additional non-limiting examples of types of nucleic acid amplification reactions include reverse transcription, in vitro transcription, ligase chain reaction, nested amplification, multiplex amplification, helicase-dependent amplification, asymmetric amplification, rolling circle amplification, multiple displacement amplification (MDA); and variants of PCR that include real-time PCR, hot start PCR, inverse PCR, methylation-specific PCR, allele-specific PCR, assembly PCR, asymmetric PCR, miniprimer PCR, multiplex PCR, nested PCR, overlap-extension PCR, digital PCR, emulsion PCR, dial-out PCR, helicase-dependent PCR, nested PCR, thermal asymmetric interlaced PCR, single-tube PCR, quantitative PCR, multiple PCR, direct PCR and touchdown PCR.

A method for nucleic acid amplification described herein may include a reverse transcription polymerase chain reaction (RT-PCR). An RT-PCR nucleic acid amplification reaction may include the use of a reverse transcriptase and a reverse transcription primer that can generate complementary DNA (cDNA) from an RNA template. The cDNA can then be amplified with appropriate forward and reverse primers and the action of polymerase in a PCR nucleic acid amplification reaction. Thus, a reaction mixture in which an RT-PCR nucleic acid amplification reaction takes place may include a reverse transcriptase. Any suitable reverse transcriptase may be used for an RT-PCR nucleic acid amplification reaction with non-limiting examples of reverse transcriptases that include HIV-1 reverse transcriptase, M-MLV reverse transcriptase, AMV reverse transcriptase, telomerase reverse transcriptase, and variants, modified products and derivatives thereof. In cases where forward and/or reverse primers or a include molecular moieties, an RT-PCR reaction mixture may also include an enzyme capable of cleaving the molecular moiety, such as, for example, an enzyme having 3' to 5' exonuclease activity, as described elsewhere herein. The presence of molecular moieties in a forward primer, reverse primer and/or reverse transcription primer of an RT-PCR amplification reaction can increase the sensitivity of an RT-PCR amplification reaction such as, for example, by inhibiting mis-priming by a reverse transcriptase.

In some embodiments, an RT-PCR nucleic acid amplification reaction can be performed in a single reaction mixture (e.g., such as a reaction mixture in a single vessel), where all reagents (e.g., RNA template, dNTPs, polymerase, reverse transcriptase, enzyme with 3' to 5' exonuclease activity, reverse transcription primer, forward primer, reverse primer, etc.) necessary to generate cDNA from an RNA template and further amplify the generated cDNA are provided in the reaction mixture. The reaction mixture can be subject to appropriate conditions (e.g., temperatures, etc.) to complete the various phases (e.g., reverse transcription of an RNA template to generate cDNA, amplification of the cDNA, etc.) of the RT-PCR amplification reaction. In some embodiments, the entire RT-PCR amplification reaction can proceed without removal or addition of further reagents or contents to the reaction mixture.

Figure 2:
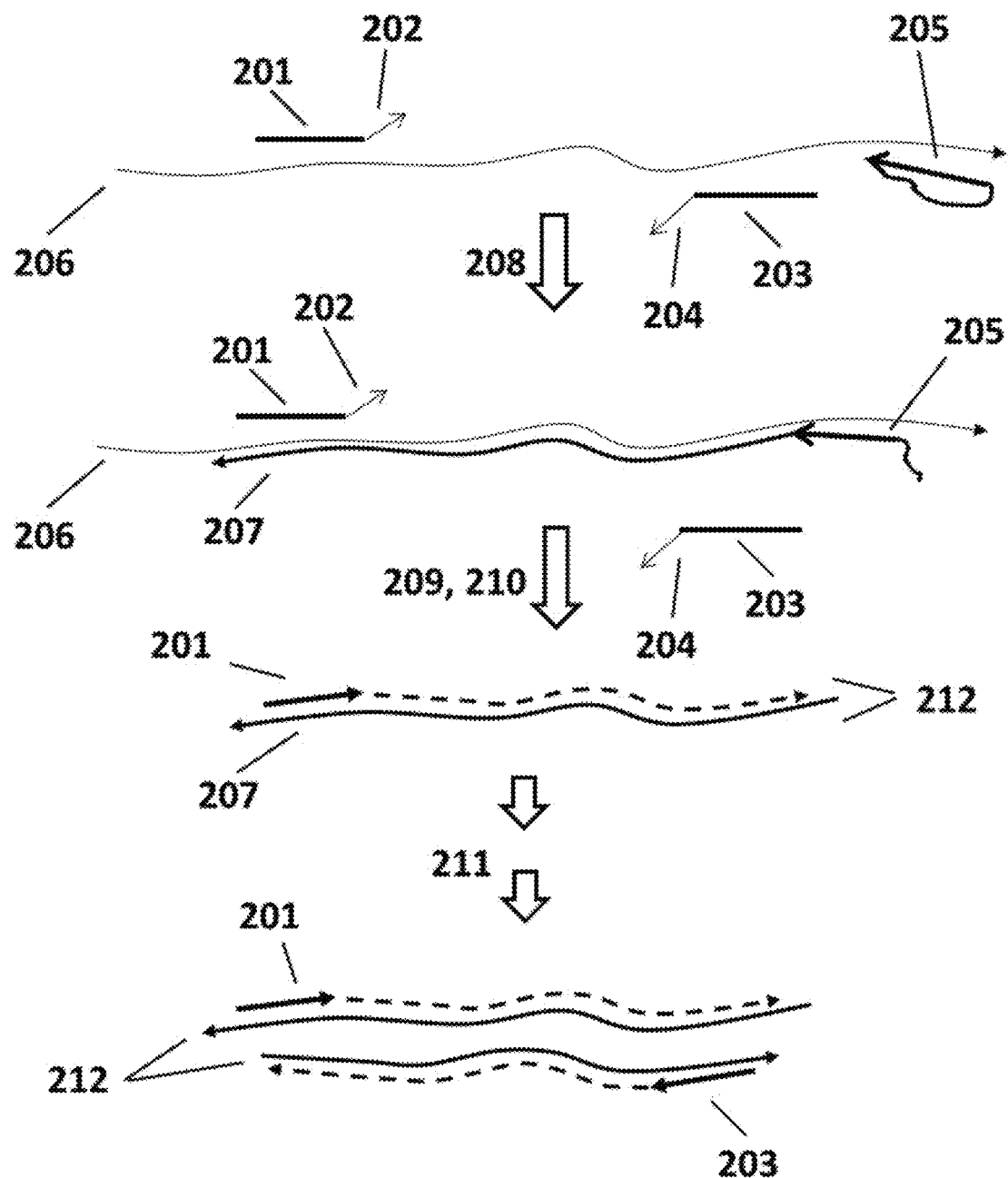
FIG. 2 is a schematic depicting an example method for nucleic acid amplification.

In some embodiments, a forward primer and/or reverse primer used in a method for nucleic acid amplification described herein may be adapted for use in an RT-PCR nucleic acid amplification reaction. An example use of forward and reverse primers comprising molecular moieties and adapted for use in an RT-PCR nucleic acid amplification reaction is schematically depicted in FIG. 2. As shown in FIG. 2, a forward primer 201 comprising a molecular moiety 202, a reverse primer 203 comprising a molecular moiety 204, and a reverse transcription primer 205 are provided in a reaction mixture with an RNA template 206 along with reagents (e.g., polymerase (e.g., polymerase with 3' to 5' exonuclease activity, a polymerase with endonuclease activity), reverse transcriptase, dNTPs, co-factors, etc.) suitable for conducting an RT-PCR reaction. The reverse transcription primer 205 is configured in a hairpin structure.

Upon raising the temperature 208 of the reaction mixture to a temperature higher than the melting temperature of the reverse transcription primer 205 (e.g., the temperature at which the reverse transcription primer 205 linearizes such as, for example, a temperature higher than about 30° C.) but lower than the annealing temperature (e.g., a temperature lower than about 60° C.) of the forward and reverse primers to complementary DNA molecules, the reverse transcription primer 205 hybridizes to the RNA template 206 and the action of the reverse transcriptase in the reaction mixture generates a molecule of cDNA 207 hybridized with the RNA template 206 and that is at least partially complementary to the RNA template 206.

Upon raising the temperature 209 of the reaction mixture to an appropriate denaturation temperature (e.g., about 90° C. or greater), the RNA template 206 and cDNA molecule 207 are separated. The temperature of the reaction mixture is then lowered 210 to an annealing temperature (e.g., about 60° C. or greater) at which the forward primer anneals to the molecule of cDNA 207. At an appropriate extension temperature, the action of a polymerase with 3' to 5' exonuclease activity in the reaction mixture cleaves the molecular moiety 202 of forward primer 201 such that its 3' end can be extended in a primer extension reaction via the action of the polymerase to generate a double-stranded DNA molecule 212.

The double-stranded DNA molecule 212 can be denatured into its component strands and subject to multiple cycles 211 of denaturation, annealing and extension temperatures as described above (e.g., such as multiple cycles of a PCR amplification reaction) to generate additional double-stranded DNA molecules 212. During each cycle the forward primer 201 can hybridize with its respective strand of double-stranded DNA molecule 212, its molecular moiety cleaved via the 3' to 5' exonuclease activity of the polymerase, and its 3' end extended via the action of the polymerase. Similarly, during each cycle, the reverse primer 203 can hybridize with its respective strand of double-stranded DNA molecule 212, its molecular moiety cleaved (e.g., via the 3' to 5' exonuclease activity of the polymerase), and its 3' end extended via the action of the polymerase. Extension of both the forward primer 201 and reverse primer 203 generates additional double-stranded DNA molecules 212.

In various aspects described herein, a method may comprise detecting one or more nucleic acid molecules described herein, such as, for example amplified double-stranded target nucleic acid molecules, amplified products of a nucleic acid sample, amplified products of a target nucleic acid molecule, double-stranded nucleic acid molecules, single-stranded nucleic acid molecules, target nucleic acid molecules, forward primers, reverse primers, and/or primer dimer molecular complexes or by-products. In some embodiments, a method described herein may comprise detecting at least a subset of amplified double-stranded target nucleic acid molecules, amplified products of a nucleic acid sample, or amplified products of a target nucleic acid molecule. Detection of any type of nucleic acid molecule described herein may be achieved via any suitable detection method or modality. The particular type of detection method or modality used may depend, for example, on the particular species being detected, other species present during detection, whether or not a detectable species is present, the particular type of detectable species to-be-used and/or the particular application.

Non-limiting examples of detection methods include optical detection, spectroscopic detection, electrostatic detection and electrochemical detection. Accordingly, a nucleic acid molecule described herein may be detected by detecting signals (e.g., signals indicative of an optical property, a spectroscopic property, an electrostatic property or an electrochemical property of the nucleic acid molecule or an associated detectable species) that are indicative of the presence or absence of the nucleic acid molecule. Optical detection methods include, but are not limited to, visual inspection (e.g., detection via the eye, observing an optical property or optical event without the aid of an optical detector), fluorimetry, chemiluminescence imaging, fluorescence resonance energy transfer (FRET) and UV-vis light absorbance. Spectroscopic detection methods include, but are not limited to, mass spectrometry, nuclear magnetic resonance (NMR) spectroscopy, Raman spectroscopy, and infrared spectroscopy. Electrostatic detection methods include, but are not limited to, gel based techniques, such as, for example, gel electrophoresis (e.g., agarose gel or polyacrylamide gel electrophoresis). Gel electrophoresis methods can separate different nucleic acid molecules in a reaction mixture based on the molecular size of the nucleic acid molecules. The separation profile (e.g., sizes of various nucleic acids in a reaction mixture) can be used to identify nucleic acid molecules subject to gel electrophoresis according to their molecular sizes. Electrochemical detection methods include, but are not limited to, amperometry.

In some embodiments, detection of a nucleic acid molecule described herein may be achieved with the aid of a detectable species. A detectable species may be linked or coupled with a nucleic acid molecule covalently and/or non-covalently (e.g., including intercalation of a double-stranded nucleic acid molecule). Moreover, a detectable species may be included in a reaction mixture that is used for nucleic acid amplification, as described elsewhere herein. In some embodiments, a method for nucleic acid amplification described herein may include a real-time nucleic acid amplification reaction (e.g., real time PCR reaction) whereby amplification products are detected during or after the amplification of a nucleic acid molecule. Non-limiting examples of detectable species include optically-responsive species (e.g., optically-responsive dyes, optically-responsive oligonucleotide probes (e.g., TaqMan probes, TaqMan Tamara probes, TaqMan MGB probes, Lion probes, molecular beacons)) and radiolabels (e.g., $^{14}C$, $^{123}I$, $^{124}I$, $^{125}I$, $^{131}I$, $^{99m}Tc$, $^{35}S$, or $^{3}H$).

In some embodiments, a detectable species may be an optically-responsive dye. (e.g., a fluorescent dye) that generates (or fails to generate a signal) when subjected to the appropriate conditions. Non-limiting examples of dyes include SYBR green, SYBR blue, DAPI, propidium iodine, Hoeste, SYBR gold, EvaGreen, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), SYBR Green, Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2(and 3)-5-(Acetylmercapto)-succinyl]amino} fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

An additional method of detection that can be used to detect a nucleic acid molecule described herein is a melting curve analysis. In particular, a melting curve analysis may be useful in detecting primer dimer molecular complexes or by-products and/or single nucleotide polymorphisms, as described elsewhere herein. In a melting curve analysis, a mixture (e.g., an amplification reaction mixture) comprising double-stranded nucleic acid molecules can be heated and dissociation (e.g., denaturing) of the double-stranded nucleic acid molecules in the mixture can be measured against temperature. The temperature-dependent dissociation of strands of a double-stranded nucleic molecule can be measured using a detectable species (e.g., a fluorophore such as, for example SYBR green or EvaGreen, nucleic acid probes labelled with a detectable species) that can intercalate or bind double-stranded nucleic acid molecules. For example, in the case of an intercalator (e.g., SYBR green) that fluoresces when bound to a double-stranded nucleic acid molecule, the dissociation of double-stranded nucleic acid molecules during heating can be determined by a reduction in fluorescence that results. A reduction in fluorescence can result due to the release of an intercalating dye from a dissociated double-stranded nucleic acid molecule. The free dye may not fluoresce (or may not fluoresce at the same wavelength as the bound species) and thus, a reduction in fluorescence may be used to indicate a dissociation of double-stranded nucleic acid molecules. The first derivative or negative first derivative of dissociation (e.g., negative first derivative of fluorescence) as a function of temperature may be plotted to determine a temperature of dissociation (e.g., temperature at which 50% dissociation occurs) via peaks in the plot. A nucleic acid molecule may be identified via the obtained dissociation profile and/or temperature of dissociation.

Moreover, an amplified nucleic acid molecule described herein (e.g., including an amplified product of a target nucleic acid molecule, an amplified product of a nucleic acid sample, and an amplified double-stranded target nucleic acid molecule described elsewhere herein) may be detected at varied specificity over other nucleic acid molecules after a given number of amplification cycles. For example, specificity may depend on the particular primers used for amplification, nucleic acid molecule to be amplified, and/or other species in an amplification reaction mixture. An example measure of amplification specificity is the cycle threshold (Ct) for an amplification product during an amplification reaction, as described elsewhere herein. In some embodiments, Ct value can be anywhere between the total number of cycles of a given amplification reaction and any number above background level. In some embodiments, Ct value can be inversely proportional to the initial amount of a nucleic acid molecule to be amplified. For example, the cycle threshold for an amplified nucleic acid molecule obtained using a method for nucleic acid amplification described herein may be detected at a Ct value of less than 80, 75, 70, 65, 60, 55, 50, 45, 40, 35, 30, 25, 20, 15, 10, 5 or less.

Methods for nucleic acid amplification may be suitable for use in single nucleotide polymorphism (SNP) detection. In some embodiments, a forward primer and/or reverse primer used in a method for nucleic acid amplification described herein may be suitable for use in SNP detection. A forward primer and/or reverse primer may comprise a molecular moiety comprising a screening nucleotide that has an unnatural base (e.g., hypoxanthine in inosine, uracil) that can better base pair with a preferred complement nucleotide in a SNP site than the alternative complement nucleotide of the SNP.

In the presence of an enzyme with proofreading activity (e.g., a polymerase with 3' to 5' exonuclease activity) and when the screening nucleotide of a primer is base-paired to its preferred nucleotide at the SNP site under interrogation on a target nucleic acid molecule, the primer can be extended by a polymerase. Primer extension can generate copies that contain the screening nucleotide, which copies may not be subsequently copied efficiently by the polymerase in additional cycles of nucleic acid amplification due to the presence of the unnatural base in the screening nucleotide. Such a scenario can result in a relatively low level of amplification of the target nucleic acid molecule.

In the presence of an enzyme with proofreading activity (e.g., a polymerase with 3' to 5' exonuclease activity) and when the screening nucleotide of a primer is base-paired to its non-preferred nucleotide at the SNP site under interrogation on a target nucleic acid molecule, the screening nucleotide can be removed from the primer via the 3' to 5' exonuclease of the polymerase and replaced with a nucleotide comprising a base corresponding to the natural complement of the non-preferred nucleotide of the target nucleic acid molecule at the SNP site. Primer extension can generate copies that contain the nucleotide with the natural complement base, which can then be subsequently copied in additional rounds of nucleic acid amplification. Such a scenario can result in preferential amplification of target nucleic acid molecules comprising the screening nucleotide's non-preferred complement nucleotide in the SNP site. Preferential amplification can be detected by detecting the level of amplification products (e.g., via any suitable detection method including example detection methods described herein) used to determine that the non-preferred nucleotide of the screening nucleotide is the nucleotide in the SNP site.

In order to interrogate a nucleic acid sample for a particular SNP, the nucleic acid sample may be split into two reaction mixtures that each comprises a forward and/or reverse primer comprising a screening nucleotide for a particular nucleotide of a SNP. The particular screening nucleotide present in the reaction mixture with the higher level of amplification products can then be used to determine the particular nucleotide in the SNP site of the nucleic acid sample.

Figure 3:
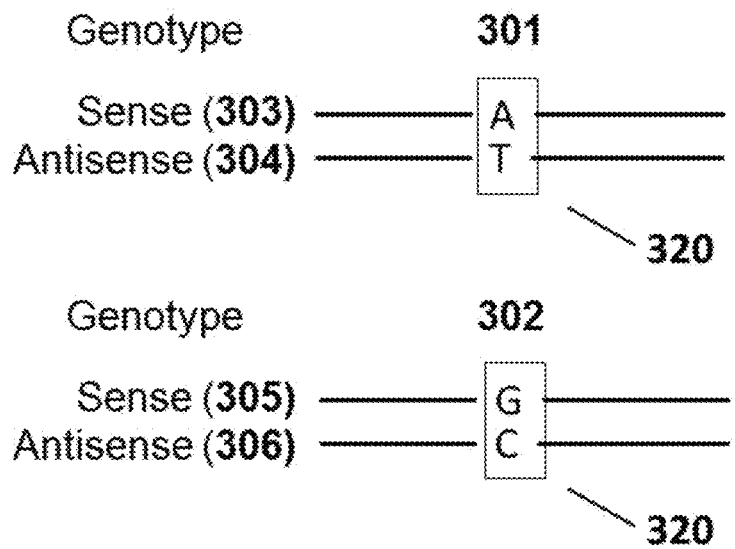
FIG. 3 (panel A) is a schematic depicting an example single nucleotide polymorphism (SNP) in a nucleic acid molecule.
Figure 3:
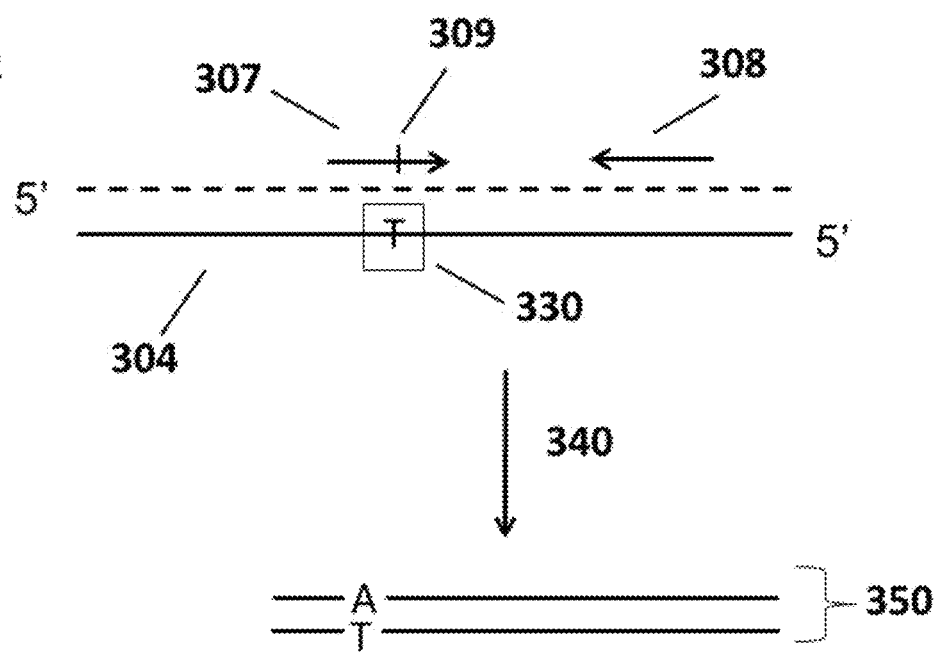
Figure 3:
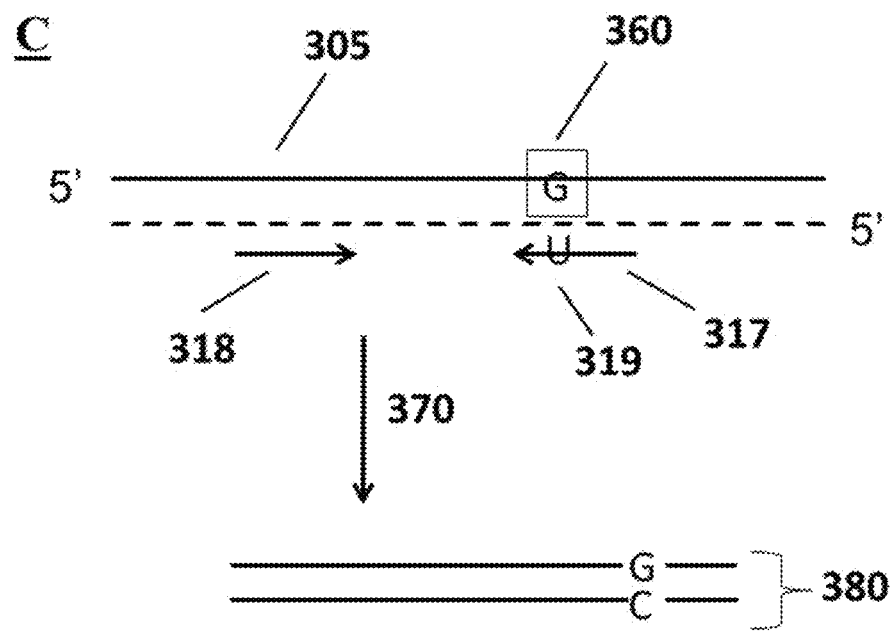

An example of detecting two genotypes corresponding to a SNP site in a target nucleic acid molecule is schematically depicted in FIG. 3A-3C. As shown in FIG. 3A, a particular target nucleic acid may have a SNP site 320 that in a first genotype 301 comprises an adenine containing nucleotide ("A") in its sense strand 303 and a thymine containing nucleotide ("T") in its antisense strand 304. In a second genotype 302, the target nucleic acid molecule comprises a guanine containing nucleotide ("G") in its sense strand 305 and a cytosine containing nucleotide ("C") in its antisense strand in the SNP site 320.

To detect first genotype 301, the target nucleic acid can be provided in a reaction mixture along with a forward primer 307, a reverse primer 308, a polymerase (e.g., Pfu polymerase) comprising 3' to 5' exonuclease activity and other reagents necessary for amplification of the target nucleic acid molecule as depicted schematically in FIG. 3B. As shown in FIG. 3B, both the forward primer 307 and reverse primer 308 can comprise a molecular moiety that can be cleaved via the 3' to 5' exonuclease activity of the polymerase. The molecular moieties of the forward primer 307 and reverse primer 308 can aid in minimizing the generation of primer dimer molecular complexes or by-products during amplification of the target nucleic acid molecule. In its molecular moiety, the forward primer 307 can comprise an inosine screening nucleotide 309 ("I") that can be removed by the polymerase with 3' to 5' exonuclease activity when bound to the thymine containing nucleotide in the SNP site 330 of the antisense strand 304 of the target nucleic acid molecule.

The inosine screening nucleotide 309 comprises a hypoxanthine base that generally binds better with a cytosine containing nucleotide (a "preferred" complement nucleotide of the inosine screening nucleotide 309) than the thymine containing nucleotide (a "non-preferred" complement nucleotide of inosine screening nucleotide 309) at the SNP site 330 of antisense strand 304 of the target nucleic acid molecule. Due to the relatively weak binding of the inosine screening nucleotide 309 and thymine containing nucleotide of the antisense strand 304 of the target nucleic acid molecule, the 3' to 5' exonuclease activity of the polymerase can remove the inosine screening nucleotide 309 from the forward primer 307 during cleavage of the molecular moiety of forward primer 307. Following cleavage of the molecular moiety from the forward primer 307, the polymerase can then extend the 3' end of the forward primer 307 such that the natural complement nucleotide (adenine-containing nucleotide "A") of the thymine containing nucleotide in the SNP site 330 of the antisense strand 304 is added to the forward primer 307 at the SNP site 330.

The temperature of the reaction mixture is cycled through annealing and extension temperatures as described elsewhere herein such that the forward primer 307 anneals to the antisense strand 304 of the target nucleic acid molecule, the molecular moiety comprising the inosine screening nucleotide 309 is removed via the 3' to 5' exonuclease activity of the polymerase, and the 3' end of the forward primer 307 is extended. Extension can result in the generation of an amplified double-stranded nucleic acid molecule comprising an adenine containing nucleotide in place of the inosine screening nucleotide 309 in the sense strand SNP site of double-stranded nucleic acid molecule. Since the inosine screening nucleotide 309 is removed by the polymerase, the double-stranded nucleic acid molecule can then be subject to multiple cycles of amplification 340 using the forward primer 307 and reverse primer 308 to generate additional amplified double-stranded nucleic acid molecules 350. The amplified double-stranded nucleic acid molecules 350 can be detected and the genotype of the target nucleic acid molecule determined to be genotype 301 based on the presence of amplified double-stranded nucleic acid molecules 350.

To detect second genotype 302, the target nucleic acid can be provided in a reaction mixture along with a forward primer 317, a reverse primer 318, a polymerase (e.g., Pfu polymerase) comprising 3' to 5' exonuclease activity and other reagents necessary for amplification of the target nucleic acid molecule as depicted schematically in FIG. 3C. As shown in FIG. 3C, both the forward primer 317 and reverse primer 318 can comprise a molecular moiety that can be cleaved via the 3' to 5' exonuclease activity of the polymerase. The molecular moieties of the forward primer 317 and reverse primer 318 can aid in minimizing the generation of primer dimer molecular complexes or by-products during amplification of the target nucleic acid molecule. In its molecular moiety, the forward primer 317 can comprise an uracil containing screening nucleotide 319 ("U") that can be removed by the polymerase with 3' to 5' exonuclease activity when bound to the guanine containing nucleotide in the SNP site 360 of the sense strand 305 of the target nucleic acid molecule.

The uracil containing screening nucleotide 319 comprises a uracil base that generally binds better with an adenine containing nucleotide (a "preferred" complement nucleotide of the uracil containing screening nucleotide 319) than the guanine containing nucleotide (a "non-preferred" complement nucleotide of uracil containing screening nucleotide 319) at the SNP site 360 of sense strand 305 of the target nucleic acid molecule. Due to the relatively weak binding of the uracil containing screening nucleotide 319 and guanine containing nucleotide of the sense strand 305 of the target nucleic acid molecule, the 3' to 5' exonuclease activity of the polymerase can remove the uracil containing screening nucleotide 319 from the forward primer 317 during cleavage of the molecular moiety of forward primer 317. Following cleavage of the molecular moiety from the forward primer 317, the polymerase can then extend the 3' end of the forward primer 317 such that the natural complement nucleotide (cytosine-containing nucleotide "C") of the guanine containing nucleotide in the SNP site 360 of the sense strand 305 is added to the forward primer 317 at the SNP site 360.

The temperature of the reaction mixture is cycled through annealing and extension temperatures as described elsewhere herein such that the forward primer 317 anneals to the sense strand 305 of the target nucleic acid molecule, the molecular moiety comprising the uracil containing screening nucleotide 319 is removed via the 3' to 5' exonuclease activity of the polymerase, and the 3' end of the forward primer 317 is extended. Extension can result in the generation of an amplified double-stranded nucleic acid molecule comprising a cytosine containing nucleotide in place of the uracil containing screening nucleotide 319 in the antisense strand SNP site of double-stranded nucleic acid molecule. Since the uracil containing screening nucleotide 319 is removed by the polymerase, the double-stranded nucleic acid molecule can then be subject to multiple cycles of amplification 370 using the forward primer 317 and reverse primer 318 to generate additional amplified double-stranded nucleic acid molecules 380. The amplified double-stranded nucleic acid molecules 380 can be detected and the genotype of the target nucleic acid molecule determined to be genotype 302 based on the presence of amplified double-stranded nucleic acid molecules 380.

The example methods for detecting genotypes 301 and 302 shown in FIGS. 3A-3C can be used simultaneously to detect the particular genotype in a nucleic acid sample. The nucleic acid sample can be split and provided to two amplification reaction mixtures. In addition to an appropriate reverse primer, a polymerase with 3' to 5' exonuclease activity and other reagents necessary to amplify a target nucleic acid molecule in the nucleic acid sample, each of the reaction mixtures can comprise either forward primer 307 or forward primer 317. The reaction mixtures can then be subject to conditions suitable to amplify the target nucleic acid molecule in the nucleic acid sample. The relative levels of amplification products (corresponding to amplification via forward primer 307 or forward primer 317) in each reaction mixture can be used together to determine which genotype is present in the original nucleic acid sample. If the reaction mixture comprising forward primer 307 generates a higher level of amplification products than the reaction mixture comprising forward primer 317, then it can be generally determined that the nucleic acid sample comprises genotype 301. If the reaction mixture comprising forward primer 317 generates a higher level of amplification products than the reaction mixture comprising forward primer 307, then it can be generally determined that the nucleic acid sample comprises genotype 302.

Additionally, a primer (e.g., a forward primer, a reverse primer) described herein can be comprise one or more stopper or blocker nucleotides that can inhibit or impair the activity of an enzyme having 3' to 5' exonuclease activity. Such a primer can be useful, for example, in the detection of a SNP, point mutation, specific junction from deletion, insertion or translocation, and/or HLA typing. For example, a forward primer and/or a reverse primer used to detect a SNP in an amplification reaction may comprise one or more stopper or blocker nucleotides. In some embodiments, the screening nucleotide of a forward or reverse primer may also be a stopper or blocker nucleotide. Examples forward primers with different screening nucleotides that comprise molecular moieties and stopper or blocker nucleotides are depicted in FIG. 12A (screening nucleotide an adenine-containing nucleotide "A") and FIG. 12B (screening nucleotide a guanine-containing nucleotide "G").

Figure 12:
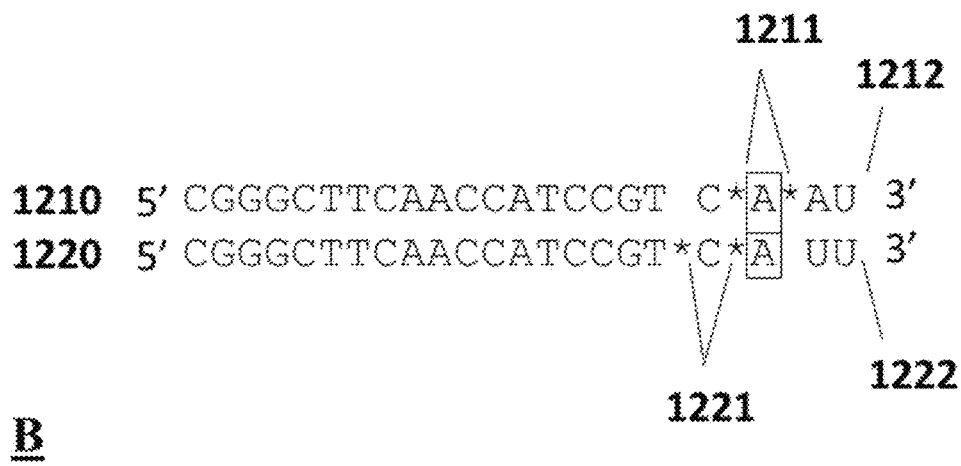
FIG. 12 (panel A) and FIG. 12 (panel B) depict example forward primers (SEQ ID NOS: 38-41, respectively, in order of appearance) suitable for use in detecting a single nucleotide polymorphism (SNP).
Figure 12:
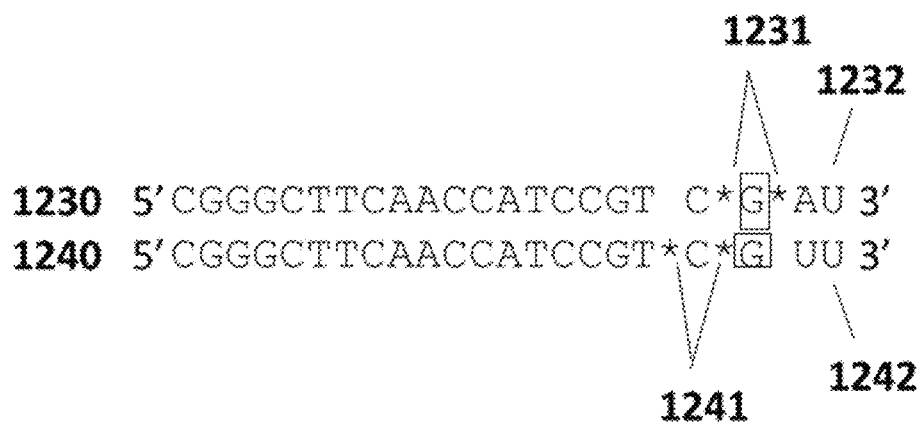

FIG. 12A shows two different example forward primers 1210 and 1220. Forward primer 1210 and 1220 both comprise an "A" screening nucleotide (indicated in a box) but differ in their molecular moieties 1212 and 1222, respectively. Molecular moiety 1212 comprises a sequence of "U" and molecular moiety 1222 comprises a sequence of "UU". Moreover, the positioning of the stopper or blocker nucleotides 1211 (for forward primer 1210, indicated with a "*" before the nucleotide in the sequence shown in 1210) and 1221 (for forward primer 1220, indicated with a "*" before the nucleotide in the sequence shown in 1220) differs between the two forward primers 1210 and 1220. In forward primer 1210, the stopper or blocker nucleotides 1211 include the screening nucleotide and an additional adenine-containing nucleotide 3' to the screening nucleotide (e.g., *A*A). In forward primer 1220, the stopper or blocker nucleotides 1221 include the screening nucleotide and an additional cytosine-containing nucleotide 5' to the screening nucleotide (e.g., *C*A). In both forward primers 1210 and 1220, the screening nucleotide also functions as a stopper or blocker nucleotide.

FIG. 12B shows two different example forward primers 1230 and 1240. Forward primer 1230 and 1240 both comprise a "G" screening nucleotide (indicated in a box) but differ in their molecular moieties 1232 and 1242, respectively. Molecular moiety 1232 comprises a sequence of "U" and molecular moiety 1242 comprises a sequence of "UU". Moreover, the positioning of the stopper or blocker nucleotides 1231 (for forward primer 1230, indicated with "*" before the nucleotide in the sequence shown in 1230) and 1241 (for forward primer 1240, indicated with "*" before the nucleotide in the sequence shown in 1240) differs between the two forward primers 1230 and 1240. In forward primer 1230, the stopper or blocker nucleotides 1231 include the screening nucleotide and an additional adenine-containing nucleotide 3' to the screening nucleotide (e.g., *G*A). In forward primer 1240, the stopper or blocker nucleotides 1241 include the screening nucleotide and an additional cytosine-containing nucleotide 5' to the screening nucleotide (e.g., *C*G). In both forward primers 1230 and 1240, the screening nucleotide also functions as a stopper or blocker nucleotide.

Additional applications in which a method for nucleic acid amplification (e.g., using forward and reverse primers with molecular moieties) described herein may be suitable include genotyping detection, HLA typing, nucleic acid amplification without purification, single-vessel amplification reactions (e.g., RT-PCR amplification reactions), mutation detection, gene expression detection, low quantity nucleic acid detection, viral stain/subtype detection, bacterial drug resistance detection and transgenic organism detection.

EXAMPLES

Example 1: Nucleic Acid Amplification Via Primers with Molecular Moieties

Nucleic acid comprising a complementary sequence for the human Epidermal Growth Factor Receptor (EGFR) gene (complementary sequence shown in FIG. 4A) was amplified with a forward primer and a reverse primer in six different amplification reaction mixtures (1-6). Each of the six reaction mixtures included one of four forward primers ("EG5", "EG5A", "EG5U" or "EG5T") and one of two reverse primers ("EG3" or "EG3A") shown in FIG. 4B, with different reaction mixtures comprising a different combination of forward and reverse primers. The combination of forward and reverse primers in each reaction mixture is shown in FIG. 4C, with each reaction mixture entered into the table at the intersection of its corresponding forward and reverse primer.

The various forward and reverse primers differed from each other based on the presence of a molecular moiety and the composition of any molecular moiety present. With respect to the specific forward primers, forward primer EG5 did not have an attached molecular moiety; forward primer EG5A had a molecular moiety at its 3' end of the sequence "UTT TTT T"; forward primer EG5U had a molecular moiety at its 3' end of the sequence "UUU"; and forward primer EG5T had a molecular moiety at its 3' end of the sequence "TTT". With respect to the specific reverse primers, reverse primer EG3 did not have an attached molecular moiety and reverse primer EG3A had a molecular moiety at its 3' end of the sequence "U TTT TTT."

Each reaction mixture had a total volume of 20 microliters ("µL"). Each reaction mixture included about 1 nanogram (ng) of complementary EGFR DNA and also included 1× Phusion flash PCR reagent (made from 2× master mix from New England Biolabs). The concentration of the respective forward and reverse primers in each reaction mixture was 0.5 micromolar ("µM"). To complete amplification of the complementary EGFR DNA, each reaction mixture was subject to a thermal cycling program that included an initial denaturation step at 98° C. for 10 s, followed by 45 cycles of 98° C. for 1 s, 65° C. for 5 s and 72° C. for 10 s. After the thermal cycling program was completed, 10 µL each reaction mixture was analyzed with 2% agarose gel electrophoresis in the presence of Ethidium bromide. A photograph depicting the gel electrophoresis analysis is shown in FIG. 4D.

Figure 4:
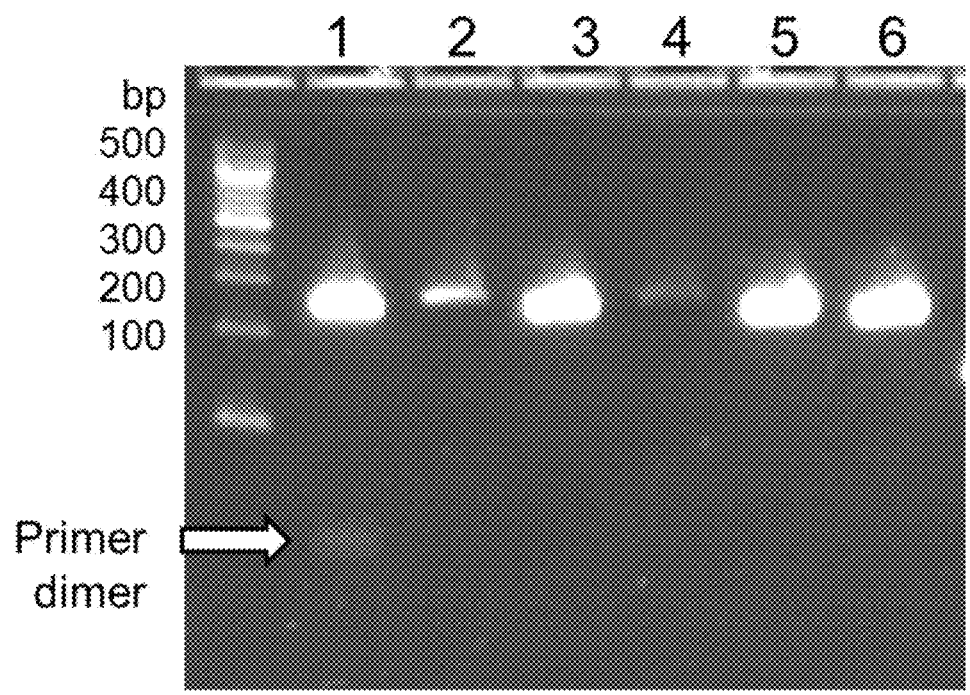
FIG. 4 (panel A) is an example target nucleic acid sequence (SEQ ID NO: 1) as described in Example 1.

As shown in FIG. 4D, amplification products were observed in all six reaction mixtures. However, primer dimer molecular by-products were observed when forward and reverse primers (e.g., forward primer EG5 and reverse primer EG3) did not have associated molecular moieties (reaction mixture 1). In reactions mixtures 2-6, the forward primer or both the forward and reverse primers included a molecular moiety. In each case, amplification products were observed without associated primer dimer by-products. As shown in FIG. 4D, the generation of primer dimer by products can be minimized when using one or more primers with an associated molecular moiety. Moreover, the results in FIG. 4D also indicate that a molecular moiety associated with a forward or reverse primer can include at least six nucleotides.

Example 2: Nucleic Acid Amplification Via Primers with Molecular Moieties Having Nucleotides with Unnatural Bases Genomic nucleic acid comprising a sequence for the human Epidermal Growth Factor Receptor (EGFR) gene was amplified with a forward primer and a reverse primer in six different amplification reaction mixtures. Each of the ten reaction mixtures (00, 0C, 0G, 10, 1C, 1G, 20, 2C, 2G, 30) included one of four forward primers ("EG21e5", "EG21e5U1", "EG21e5U2" or "EG21e5U3") and one of three reverse primers ("EG21e3", "EG21e3_iso-dC" or "EG21e3_iso-dG") shown in FIG. 5A, with different reaction mixtures comprising a different combination of forward and reverse primers. The combination of forward and reverse primers in each reaction mixture is shown in FIG. 5B, with each reaction mixture entered into the table at the intersection of its corresponding forward and reverse primer.

The various forward and reverse primers differed from each other based on the presence of a molecular moiety and the composition of any molecular moiety present. In some cases, a molecular moiety included a nucleotide with an unnatural base such as iso-dC or iso-dG. With respect to the specific forward primers, forward primer EG21e5 did not have an attached molecular moiety; forward primer EG21e5U1 had a molecular moiety at its 3' end of the sequence "U"; forward primer EG21e5U2 had a molecular moiety at its 3' end of the sequence "UU"; and forward primer EG21e5U3 had a molecular moiety at its 3' end of the sequence "UU U". With respect to the specific reverse primers, reverse primer EG21e3 did not have an attached molecular moiety; reverse primer EG21e3_isodC had a molecular moiety at its 3' end of the sequence "iso-dC"; and reverse primer EG21e3_isodG had a molecular moiety at its 3' end of the sequence "iso-dG."

Each reaction mixture had a total volume of 20 µL. Each reaction mixture included about 1 nanogram (ng) of complementary EGFR DNA and also included 1× Phusion flash PCR reagent (made from 2× master mix from New England Biolabs). The concentration of the respective forward and reverse primers in each reaction mixture was 0.5 µM. To complete amplification of the genomic DNA, each reaction mixture was subject to a thermal cycling program that included an initial denaturation step at 98° C. for 10 s, followed by 45 cycles of 98° C. for 1 s, 60° C. for 10 s and 72° C. for 20 s. After the thermal cycling program was completed, 10 µL each reaction mixture was analyzed with 2% agarose gel electrophoresis in the presence of Ethidium bromide. A photograph depicting the gel electrophoresis analysis is shown in FIG. 5C.

Figure 5:
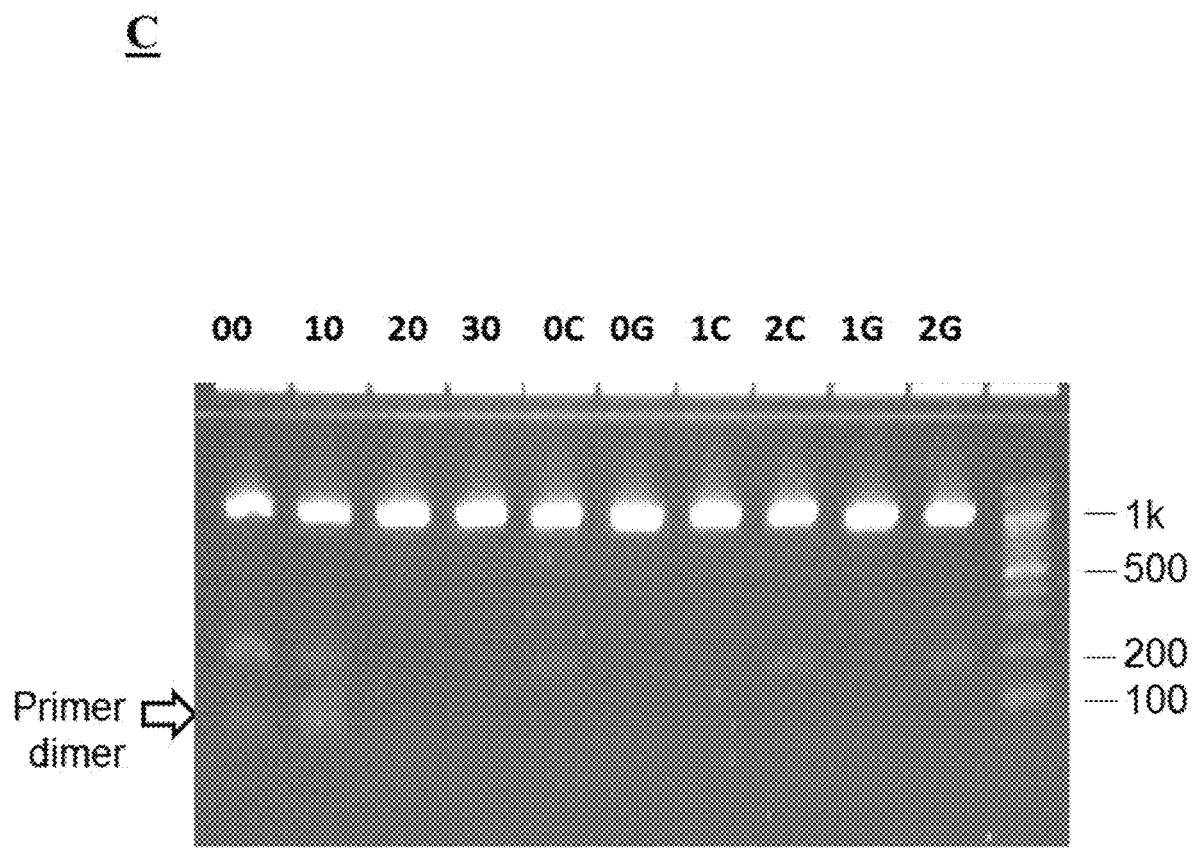
FIG. 5 (panel A) provides forward and reverse primers (SEQ ID NOS 8-14, respectively, in order of appearance) as described in Example 2.

As shown in FIG. 5C, amplification products were observed in all ten reaction mixtures. However, primer dimer molecular by-products were observed when forward and reverse primers (e.g., forward primer EG21e5 and reverse primer EG21e3) did not have associated molecular moieties (reaction mixture 00) and when the forward primer (e.g., forward primer EG21e5U1) had a molecular moiety of only one base and the reverse primer did not have an associated molecular moiety (reaction mixture 10). In reactions mixtures 20, 30, 0C, 0G, 1C, 2C, 1G and 2G, the forward primer or both the forward and reverse primers included a molecular moiety. In some cases (reaction mixtures 0C, 1C, 2C 0G, 1G and 2G) either or both of the forward and reverse primers included an iso-dC or iso-dG molecular moiety. Regardless, amplification products were observed without associated primer dimer by-products in these reaction mixtures. As shown in FIG. 5C, the generation of primer dimer by products can be minimized when using one or more primers with an associated molecular moiety. Additionally, the results shown in FIG. 5C also indicate that the length of the molecular moiety can be adjusted in order to minimize the generation of primer dimer by-products. Moreover, the results in FIG. 5C also indicate that a molecular moiety comprising nucleotide analogues with unnatural bases (e.g., iso-dC and iso-dG) can also be useful in minimizing the generation of primer dimer by-products.

Example 3: Nucleic Acid Amplification Via Primers with Molecular Moieties and Type of Polymerase(s)

Figure 6:
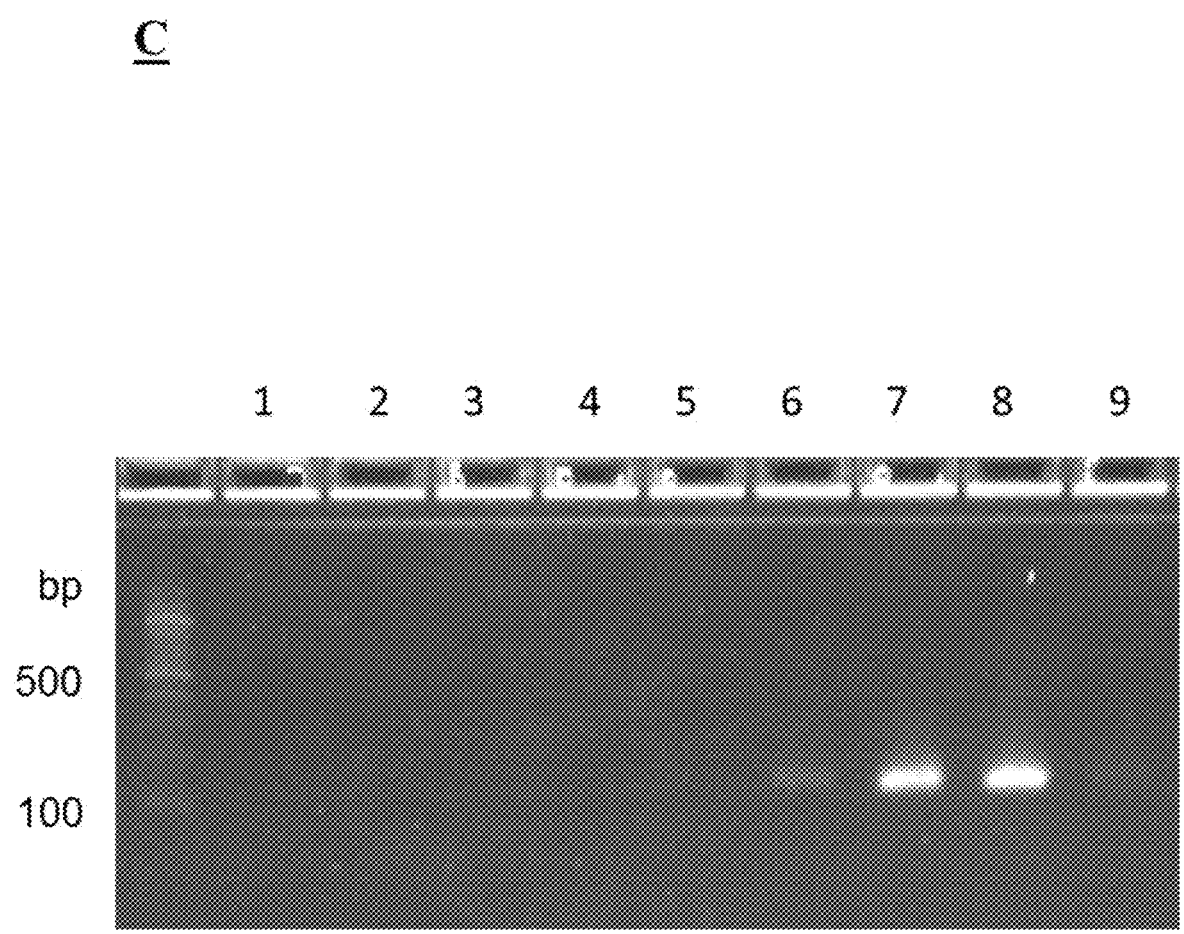
FIG. 6 (panel A) provides forward and reverse primers (SEQ ID NOS 15-16, respectively, in order of appearance) as described in Example 3.

Nucleic acid comprising a complementary sequence for the human Epidermal Growth Factor Receptor (EGFR) gene was amplified with a forward primer and a reverse primer in nine different amplification reaction mixtures. Each of the nine reaction mixtures (1-9) included forward and reverse primers with molecular moieties at their 3' ends (shown in FIG. 6A, forward primer included a molecular moiety of sequence "UU" and reverse primer included a molecular moiety of sequence "iso-dG T") and one or two polymerases (Taq, cloned Pfu, Deep vent) with different reaction mixtures comprising a different polymerase (or combination of polymerases) and/or different polymerase concentration. The polymerase(s) and concentration of polymerase(s) in each reaction mixture is shown in FIG. 6B. The polymerases tested were included a cloned Pfu polymerase control, a Deep vent polymerase (which can exhibit strong proofreading activity) and a Taq polymerase (which can exhibit strong processivity).

Each reaction mixture had a total volume of 20 μL. Each reaction mixture included about 100 copies of PCR amplified complementary EGFR DNA and also included 1× ThermoPol buffer (20 mM Tris-HCl, 10 mM $(NH_4)_2SO_4$, 10 mM KCl, 2 mM $MgSO_4$, 0.1% Triton X-100, pH 8.8 @ 25° C.) from New England Biolabs, dNTPs and the respective polymerases. The concentration of the respective forward and reverse primers in each reaction mixture was 0.5 μM and the concentration of the dNTPs was 0.25 mM. The concentration of polymerases were used as indicated in the table shown in FIG. 6B, with 1× Taq corresponding to 0.025 units/μL, 1× cloned Pfu corresponding to 0.02 units/μL (thus, 2× cloned Pfu corresponds to 0.04 units/μL and 0.25× cloned Pfu corresponds to 0.005 units/μL) and 1× Deep vent corresponding to 0.02 units/μL (thus, 2× Deep vent corresponds to 0.04 units/μL and 0.25× Deep vent corresponds to 0.005 units/μL). To complete amplification of the complementary EGFR DNA, each reaction mixture was subject to a thermal cycling program that included an initial denaturation step at 98° C. for 10 s, followed by 45 cycles of 98° C. for 5 s, 60° C. for 10 s and 72° C. for 10 s. After the thermal cycling program was completed, 10 μL each reaction mixture was analyzed with 2% agarose gel electrophoresis in the presence of Ethidium bromide. A photograph depicting the gel electrophoresis analysis is shown in FIG. 6C.

As shown in FIG. 6C, in cases where cloned Pfu was included in a reaction mixture (reaction mixtures 2-5), only Taq was included in a reaction mixture (reaction mixture 1) or only Deep vent was included in a reaction mixture (reaction mixture 9) amplification products were not observed. However, in all three reaction mixtures that included Taq and Deep vent, amplification products were observed. The results in FIG. 6C suggest that a combination of polymerases may be useful in amplifying a nucleic acid molecules with forward and reverse primers including molecular moieties. Moreover, the results in FIG. 6C also suggest that the use of a polymerase with strong proofreading activity (e.g., Deep vent) and a polymerase with strong processivity (e.g., Taq) can also aid in amplifying nucleic acid molecules with forward and reverse primers that include molecular moieties.

Example 4: Nucleic Acid Amplification Via Primers with Molecular Moieties and Annealing Times A nucleic acid comprising a target sequence (shown in FIG. 7A) was amplified with a forward primer and a reverse primer in ten different amplification reaction mixtures. Each of the ten reaction mixtures included one of three copy numbers (1, 10, 100) of the target sequence, a set of forward and reverse primers with molecular moieties at their 3' ends (forward and reverse primers shown in FIG. 7B—the primer set indicated with a "U") or a set of forward and reverse primers without molecular moieties (forward and reverse primers shown in FIG. 7B—the primer set indicated with a "N") and was subject to a thermal cycling program that included an annealing condition at 63° C. for 10 s or 20s. Both of the forward and reverse primers had molecular moieties of the sequence "UU."

Figure 7:
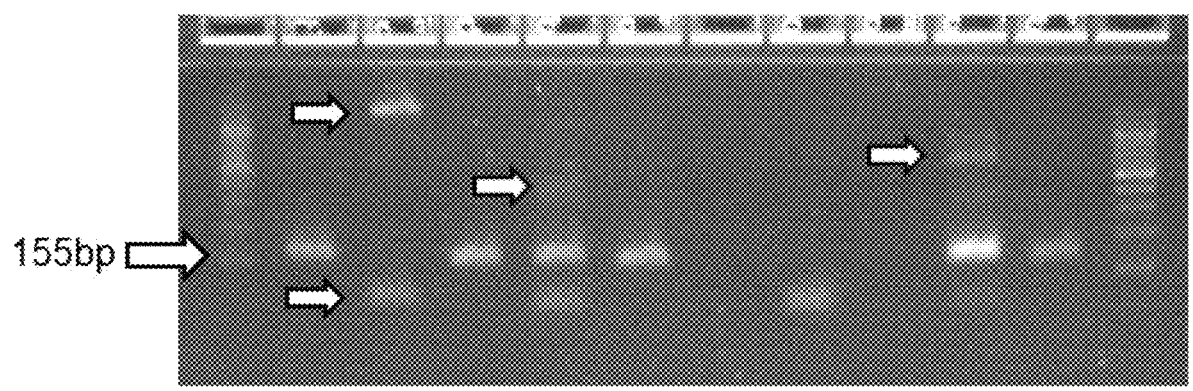
FIG. 7 (panel A) is an example target nucleic acid sequence (SEQ ID NO: 17) as described in Example 4.

Each reaction mixture had a total volume of 20 μL. Each reaction mixture included 1, 10 or 100 copies of the target sequence and also included 1× Phusion flash PCR reagent (made from 2× master mix from New England Biolabs). The concentration of the respective forward and reverse primers in each reaction mixture was 0.5 μM. To complete amplification of the target sequence, each reaction mixture was subject to a thermal cycling program that included an initial denaturation step at 98° C. for 10 s, followed by 50 cycles of 98° C. for 1 s, 63° C. for 10 s or 20 s and 72° C. for 15 s. After the thermal cycling program was completed, 10 μL each reaction mixture was analyzed with 2% agarose gel electrophoresis in the presence of Ethidium bromide. A photograph depicting the gel electrophoresis analysis is shown in FIG. 7C. The anticipated amplification product had a size of approximately 155 bp.

As shown in FIG. 7C, amplification products were generally observed with forward and reverse primers that included molecular moieties, at longer annealing times and/or in reaction mixtures with a larger initial copy number. Moreover, the generation of non-specific amplification products (e.g., products at sizes other than 155 bp in the photograph shown in FIG. 7C, indicated by arrows) was also less when forward and reverse primers that included molecular moieties were used for amplification. The results in FIG. 7C suggest that forward and reverse primers including molecular moieties can minimize the generation of non-specific amplification products and also that also that longer annealing times may also improve the efficiency of nucleic acid amplification when such forward and reverse primers are used.

Figure 8:
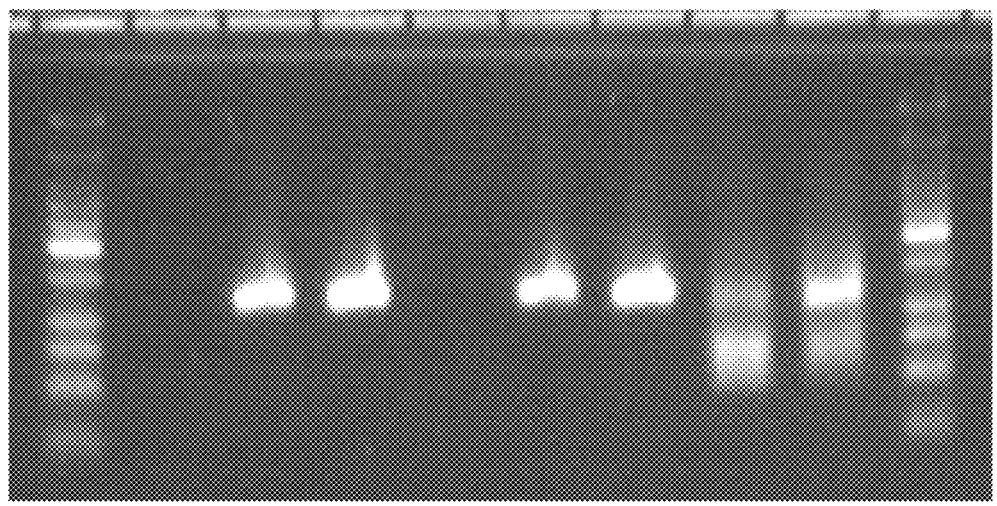
FIG. 8 (panel A) provides a table describing different test reaction mixtures as described in Example 5.

Example 5: Convection-Based Nucleic Acid Amplification Via Primers With Molecular Moieties A nucleic acid comprising a target sequence was amplified with a forward primer and a reverse primer in eight different amplification reaction mixtures. Each of the eight reaction mixtures (1-8) included a set of forward and reverse primers with molecular moieties at their 3' ends ("Primers with Molecular Moieties as shown in FIG. 8A) or a set of forward and reverse primers without molecular moieties ("Control" as shown in FIG. 8A); a detectable species (SYBR Green ("SYBR-G" as shown in FIG. 8A) or DNA probe) or no detectable species, and one of three copy numbers (0, 2 or 20) of the target sequence. Both of the forward and reverse primers with molecular moieties had molecular moieties at their 3' ends of the sequence "UU." The contents of each reaction mixture is depicted in FIG. 8A.

Each reaction mixture had a total volume of 50 μL. Each reaction mixture included 0, 2 or 20 copies of the target sequence and also included 1× Phusion flash PCR reagent (made from 2× master mix from New England Biolabs). The concentration of the respective forward and reverse primers in each reaction mixture was 0.4 μM. To complete amplification of the target sequence, each reaction mixture was subject to convection-based nucleic acid amplification. After convection-based nucleic acid amplification was completed, 10 µL each reaction mixture was analyzed with 4% agarose gel electrophoresis in the presence of Ethidium bromide. A photograph depicting the gel electrophoresis analysis is shown in FIG. 8B.

As shown in FIG. 8B, amplification products were observed for all reaction mixtures that contained the target sequence (reaction mixtures 2, 3 and 5-8). Moreover, the generation of non-specific amplification products was also greater when forward and reverse primers that did not include molecular moieties were used for amplification. The results in FIG. 8B suggest that forward and reverse primers including molecular moieties can minimize the generation of non-specific amplification products and improve the efficiency of nucleic acid amplification.

Example 6: Single-Vessel Reverse Transcription Amplification

Figure 9:
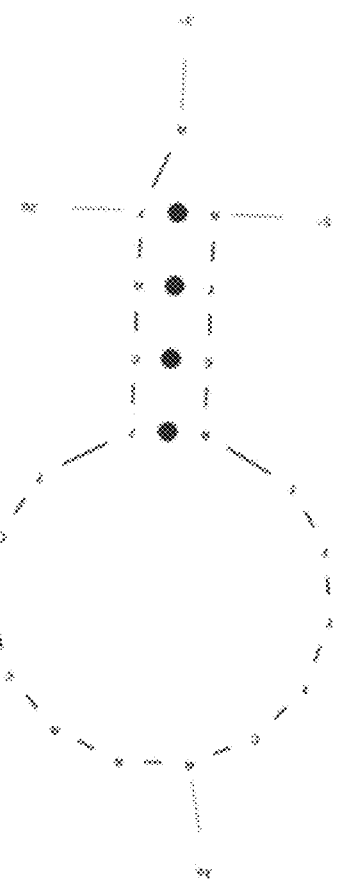
FIG. 9 (panel A) provides example target nucleic acid sequences (SEQ ID NOS: 23-25 and 29-31, respectively, in order of appearance) and corresponding example forward, reverse and reverse transcription primers (SEQ ID NOS: 22, 27, 26, 28, 32 and 26, respectively, in order of appearance) as described in Example 6.
Figure 9:
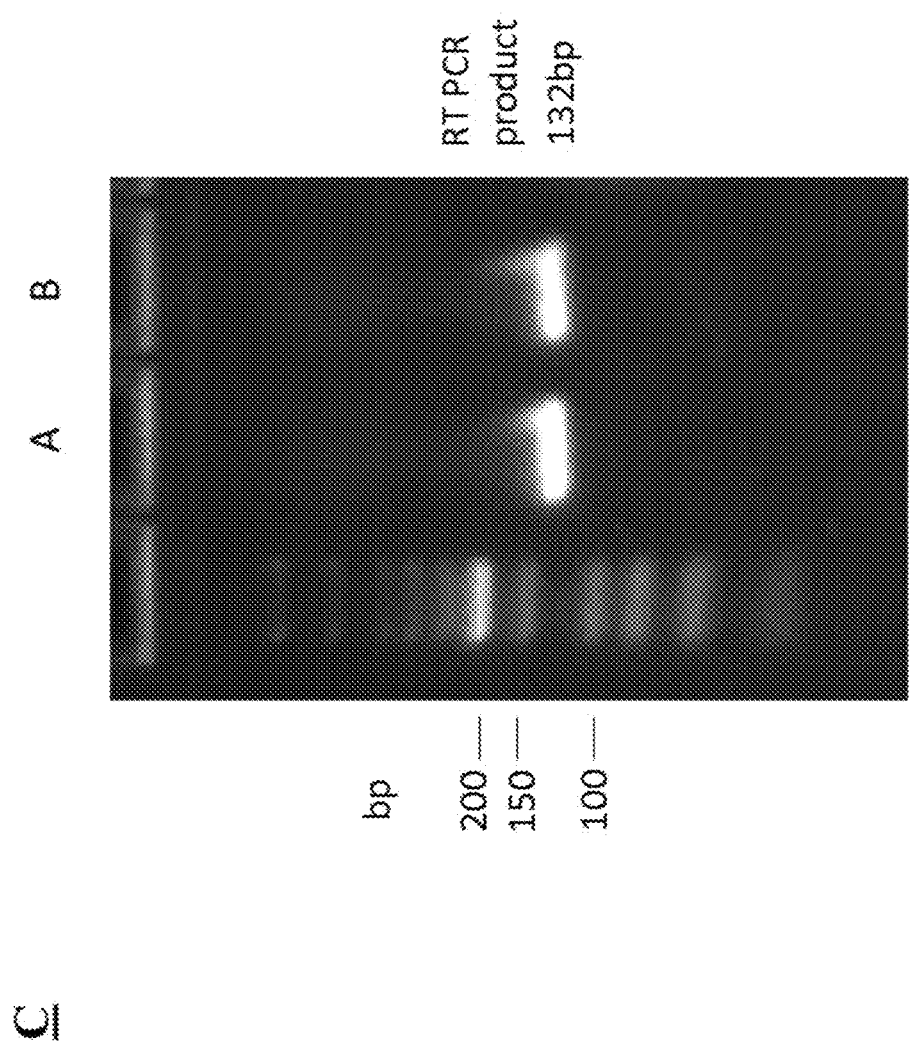

Two target RNA sequences were amplified in parallel reverse transcription amplification mixtures. The sequence for each target RNA sequence ("Target A" and "Target B") is shown in FIG. 9A. Also shown in FIG. 9A are the sequences of respective forward primers ("A forward primer" representing the forward primer for target RNA sequence A; "B forward primer" representing the forward primer for target RNA sequence B), respective reverse primers ("A reverse primer" representing the reverse primer for target RNA sequence A; "B reverse primer" representing the reverse primer for target RNA sequence B) and a reverse transcription primer ("RT primer") suitable for generating cDNA from each target RNA sequence in the presence of a reverse transcriptase.

Each forward and reverse primer included a molecular moiety having the sequence "UU" at its 3' end. The reverse transcription primer included a 21 bases, had a 24% GC content was configured as a hairpin loop primer via 4 5' bases that hybridized to a 3' region of the hairpin loop primer. A schematic depiction of the hairpin loop RT primer is shown in FIG. 9B. The stem region of the hairpin loop RT primer has a melting temperature of 30° C. and prevented extension of the hairpin loop RT primer at temperatures below the melting temperature.

Each target RNA sequence was amplified in a single reaction vessel. Each of the two reaction vessels included about 100 copies of the appropriate target RNA sequence, the appropriate forward and reverse primers (both at 0.25 µM), the hairpin loop RT primer at 1.25 µM (control experiments instead included a random primer), 1× ThermoPol buffer, 1.25 units/µL MMLV reverse transcriptase, 0.02 units/µL Phusion DNA polymerase and 2 mM DTT. To complete amplification of the target RNA sequences, each reaction mixture was subject to a thermal cycling program that included 37° C. for 10 min, 42° C. for 10 min, 98° C. for 5 min, followed by 45 cycles of 98° C. for 2 s, 60° C. for 30 s and 72° C. for 10 s. Each reaction mixture was analyzed with gel electrophoresis in the presence of Ethidium bromide. A photograph depicting the gel electrophoresis analysis is shown in FIG. 9C. The anticipated amplification products for both target RNA sequences had a size of approximately 132 bp.

As shown in FIG. 9C, amplification products of the expected size were observed for both target RNA sequences. Reaction by-products (e.g., primer-dimer by-products) were not observed. The results in FIG. 9C suggest that forward and reverse primers including molecular moieties can, in the presence of a reverse transcription primer and reverse transcriptase, amplify a target RNA sequence.

Example 7: Nucleic Acid Amplification to Detect Single Nucleotide Polymorphisms (SNPs)

Figure 10:
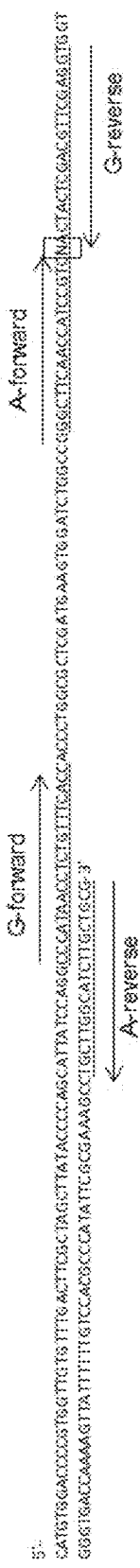
FIG. 10 (panel A) provides an example target nucleic acid sequence (SEQ ID NO: 33) with an example SNP site and associated forward and reverse primers used to interrogate the example SNP site as described in Example 7.
Figure 10:
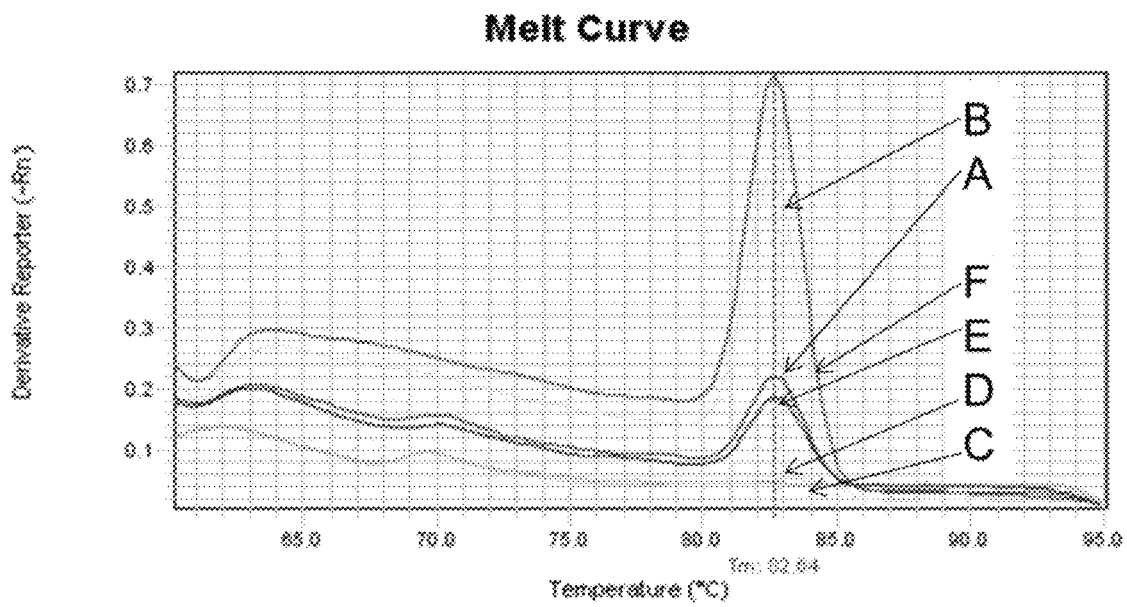
Figure 10:
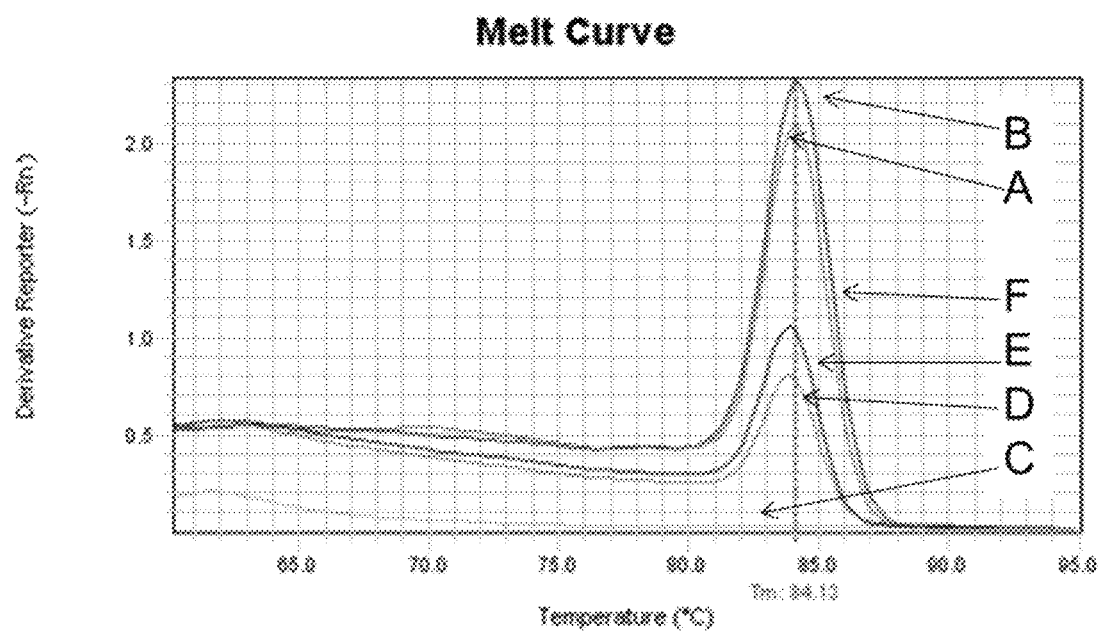

The capability of a nucleic acid amplification reaction using forward and reverse primers with molecular moieties at their 3' ends to detect single polynucleotide morphisms (SNP) in target sequence was investigated. The target sequence that was investigated is shown in FIG. 10A, having a SNP site indicated by the "N" nucleotide in the box shown in FIG. 10A. As shown in FIG. 10B, a forward primer ("A-forward") comprising a molecular moiety at its 3'end of the sequence "IUU" was used to detect an "A/T" SNP at the SNP site N. The inosine nucleotide in the molecular moiety of the A-forward primer served as a screening nucleotide for a thymine containing nucleotide in the SNP site. The corresponding reverse primer ("A-reverse") used to detect an A/T SNP at the SNP site and comprising a molecular moiety at its 3' end of sequence "UU" is also shown in FIG. 10B.

Moreover, as shown in FIG. 10B, a reverse primer ("G-reverse") comprising a molecular moiety at its 3'end of the sequence "UUU" was used to detect an "C/G" SNP at the SNP site N. The most 5' of the 3 U nucleotides in the molecular moiety of the G-reverse primer served as a screening nucleotide for a guanine containing nucleotide in the SNP site. The corresponding forward primer ("G-forward") used to detect an C/G SNP at the SNP site and comprising a molecular moiety at its 3' end of sequence "UU" is also shown in FIG. 10B.

Each primer set (A-forward/A-reverse or G-forward/G-reverse) was evaluated in discriminating its target SNP (A/T vs. C/G) in a series of six reaction mixtures (A-F). Two of the six reaction mixtures included either 100 or 1000 copies of the target sequence in FIG. 10A with the target SNP for the primer set tested in the SNP site (e.g., "A" replaced for N in the SNP site for the A-forward/A-reverse primer set, "G" replaced for N in the SNP site for the G-forward/G-reverse primer set). The other four reaction mixtures for each set included 1000, 10000, 100000 or 1000000 copies of the target sequence in FIG. 10A with the non-target SNP for the primer set tested in the SNP site (e.g., "G" replaced for N in the SNP site for the A-forward/A-reverse primer set, "A" replaced for N in the SNP site for the G-forward/G-reverse primer set).

Each reaction mixture had a total volume of 20 µL. Each reaction mixture included the appropriate number of copies of the appropriate template (A in the SNP site or G in the SNP site), the respective forward and reverse primers at 0.25 µM, 200 µM dNTPs, 0.02 units/µL Phusion DNA polymerase and buffer from New England Biolabs, and SYBR Green (at a concentration of 0.3×) and ROX (at a concentration of 1×) fluorescent dyes obtained from Life Technologies. To complete amplification of the target sequences, each reaction mixture was subject to a thermal cycling program that included an initial denaturation step at 98° C. for 10 s, followed by 45 cycles of 98° C. for 1 s, 60° C. for 30 s and 72° C. for 10 s.

After the thermal cycling program was completed, a melting curve analysis for each reaction mixture was completed. Plots depicting the results of the melting curve analyses for each set of reaction mixtures are shown in FIG. 10C (for reaction mixtures evaluating A-forward/A-reverse) and FIG. 10D (for reaction mixtures evaluating G-forward/G-reverse). In each of FIG. 10C and FIG. 10D, a table is shown indicating which target nucleotide was in the SNP site of the target sequence and the copy number of the appropriate target sequence in each reaction mixture (A-F). In FIG. 10C and FIG. 10D, the melting curve analysis for each reaction mixture is shown in the plots with letter for each labeled curve corresponding to the appropriate reaction mixture in the table.

As shown in FIG. 10C, similar changes in fluorescence were observed during melting curve analysis for target sequences comprising an A in the SNP site at substantially lower copy numbers of the target sequence when the forward-A and reverse-A primers were used for amplification. For example, a similar change in fluorescence was observed for the reaction mixture (A) comprising 100 copies of the target sequence with A in the SNP site as was observed for the reaction mixture (E) comprising 100000 copies of the target sequence with G in the SNP site. In addition, a similar change in fluorescence was observed for the reaction mixture (B) comprising 1000 copies of the target sequence with A in the SNP site as was observed for the reaction mixture (F) comprising 1000000 copies of the target sequence with G in the SNP site. In both comparisons, about 1000 fold discrimination in detecting the target SNP was observed based on the copy numbers of each target sequence in the two reaction mixtures.

Similarly, as shown in FIG. 10D, similar changes in fluorescence were observed during melting curve analysis for target sequences comprising an G in the SNP site at substantially lower copy numbers of the target sequence when the forward-G and reverse-G primers were used for amplification. For example, a higher change in fluorescence was observed for the reaction mixture (A) comprising 100 copies of the target sequence with G in the SNP site as was observed for the reaction mixture (E) comprising 100000 copies of the target sequence with A in the SNP site. In addition, a similar change in fluorescence was observed for the reaction mixture (B) comprising 1000 copies of the target sequence with G in the SNP site as was observed for the reaction mixture (F) comprising 1000000 copies of the target sequence with A in the SNP site. In both comparisons, at least 1000 fold discrimination in detecting the target SNP was observed based on the copy numbers of each target sequence in the two reaction mixtures. Accordingly, data in both FIG. 10C and FIG. 10D suggest that forward and reverse primers comprising molecular moieties with appropriate screening nucleotides can be useful in SNP detection.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

What is claimed is:

1. A method for nucleic acid amplification, comprising:
   a) providing a forward primer and a reverse primer;
   b) annealing (1) the forward primer to a single-stranded target nucleic acid molecule and (2) the reverse primer to a complement of said single-stranded target nucleic acid molecule, wherein said at least one of the forward primer and said reverse primer from a 5' end to 3' end comprises a molecular moiety at a 3' end that is non complementary to one or more nucleotides of said single-stranded target nucleic acid molecule or said complement, and wherein said molecular moiety of said forward primer and said molecular moiety of said reverse primer do not associate with each other, wherein said molecular moiety is terminated with a hydroxyl group and comprises a nucleotide or a nucleotide analogue selected from the group consisting of an inosine, a uracil-containing nucleotide, an iso-deoxycytosine (iso-dC), an iso-deoxyguanosine (iso-dG), a diaminopurine, 2,4-difluorotoluene, 4-methylbenzimidazole, a size-expanded adenine (xA), a size-expanded guanine (xG), a size-expanded cytosine (xC), a size-expanded thymine (xT), 2-((2R, 4R, 5R)-tetrahydro-4-(hydroxy-5-(hydroxymethyl) furan-2-yl)-6-methylisoquinoline-1(2H)-thione (d5SICS), 1,4-anhydro-2-deoxy-1-C-(3-methoxy2-naphthalenyl)-(1R)-D-erythro-pentitol (dNaM), an abasic nucleotide, an acyclo nucleotide and/or combination thereof;
   c) removing said molecular moiety of said forward primer annealed to said single-stranded target nucleic acid molecule and said molecular moiety of said reverse primer annealed to said complement of said single-stranded target nucleic acid molecule using a 3' to 5' exonuclease activity of a polymerase;
   d) extending said forward primer and said reverse primer in a template-directed manner to yield double-stranded target nucleic acid molecules;
   e) denaturing said double-stranded target nucleic acid molecules to generate single-stranded target nucleic acid molecules; and
   f) repeating (b)-(e) for at least one cycle to yield amplified double-stranded target nucleic acid molecules.

2. The method of claim 1, wherein after said at least one cycle, primer dimer by-products comprising said forward primer and/or said reverse primer are present at a concentration that is less than about 10% of the amplified double-stranded target nucleic acid molecules as measured by a melting curve analysis of said amplified double-stranded target nucleic acid molecules.

3. The method of claim 1, wherein (a)-(f) are performed in a partition.

4. The method of claim 3, wherein said partition is a well or a droplet.

5. A method for nucleic acid amplification, comprising:
   subjecting a reaction mixture containing a nucleic acid sample having a single-stranded target nucleic acid molecule to a nucleic acid amplification reaction under conditions to yield an amplified product of said nucleic acid sample,
   wherein said reaction mixture comprises:
   (a) a forward primer that is complementary to said single-stranded target nucleic acid molecule and comprises a first molecular moiety at a 3' end that is non complementary to one or more nucleotides of said single-stranded target nucleic acid molecule; and
   (b) a reverse primer that is complementary to a complement of said single-stranded target nucleic acid molecule and comprises a second molecular moiety at a 3' end that is non complementary to one or more corresponding nucleotides of said complement,
   wherein said first molecular moiety and said second molecular moiety are not complementary with each other and wherein said subjecting comprises removing said first molecular moiety and said second molecular moiety using a 3' to 5' exonuclease activity of a polymerase, wherein said molecular moiety is terminated with a hydroxyl group and comprises a nucleotide or a nucleotide analogue selected from the group consisting of an inosine, a uracil-containing nucleotide, an iso-deoxycytosine (iso-dC), an iso-deoxyguanosine (iso-dG), a diaminopurine, 2,4-difluorotoluene, 4-methylbenzimidazole, a size-expanded adenine (xA), a size-expanded guanine (xG), a size-expanded cytosine (xC), a size-expanded thymine (xT), 2-((2R, 4R, 5R)-tetrahydro-4-hydroxy-5-(hydroxymethyl) furan-2-yl)-6-methylisoquinoline-1(2H)-thione (d5SICS), 1,4-anhydro-2-deoxy-1-C-(3-methoxy2-naphthalenyl)-(1R)-D-erythro-pentitol (dNaM), an abasic nucleotides, an acyclo nucleotides and/or combination thereof.

6. The method of claim 5, wherein said forward primer and/or reverse primer is a hairpin loop primer comprising a nucleic acid sequence A that exhibits sequence complementarity to (1) itself and/or (2) said first and/or second molecular moiety.

7. The method of claim 5, wherein said forward primer and/or reverse primer is adapted for use in a reverse transcription polymerase chain reaction (RT-PCR).

8. The method of claim 5, wherein said first and/or second molecular moiety is adapted to prevent the formation of a primer dimer molecular complex comprising said forward primer and/or said reverse primer.

9. The method of claim 5, wherein said first and/or second molecular moiety comprises a nucleotide analogue having an unnatural base or no base.

10. The method of claim 5, wherein said forward primer and/or reverse primer is suitable for use in single nucleotide polymorphism detection.

11. The method of claim 1, further comprising detecting at least a subset of said amplified double-stranded target nucleic acid molecules.

12. The method of claim 11, wherein said detecting is optically detecting, electrostatically detecting, or electrochemically detecting.

13. The method of claim 5, wherein said subjecting comprises extending said forward primer and said reverse primer in a template-directed manner to yield double-stranded target nucleic acid molecules.

14. The method of claim 5, wherein said forward primer and/or reverse primer is an isolated and purified nucleic acid strand.

15. The method of claim 5, wherein each of said forward primer and said reverse primer from a 5' end to 3' end comprises a nucleotide sequence A that is substantially complementary to said single-stranded target nucleic acid molecule or said complement.

16. The method of claim 15, wherein said first or second molecular moiety comprises a nucleotide sequence B having 1-10 consecutive nucleotides that are non-complementary with respect to 1-10 corresponding nucleotides of said target nucleic acid molecule or said complement.

17. The method of claim 15, wherein said nucleotide sequence A is of a length that provides sufficient complementarity with respect to said target nucleic acid molecule or said complement.

* * * * *